(12) United States Patent
Kraft

(10) Patent No.: US 10,189,616 B2
(45) Date of Patent: Jan. 29, 2019

(54) SYSTEM AND METHODS FOR THE PRODUCTION OF PERSONALIZED DRUG PRODUCTS

(76) Inventor: Daniel L. Kraft, Stanford, CA (US)

(*) Notice: Subject to any disclaimer, the term of this patent is extended or adjusted under 35 U.S.C. 154(b) by 0 days.

(21) Appl. No.: 13/210,333

(22) Filed: Aug. 15, 2011

(65) Prior Publication Data
US 2012/0041778 A1 Feb. 16, 2012

Related U.S. Application Data

(60) Provisional application No. 61/401,503, filed on Aug. 13, 2010.

(51) Int. Cl.
*G06Q 50/00* (2012.01)
*A61M 35/00* (2006.01)
(Continued)

(52) U.S. Cl.
CPC .......... *B65D 51/2828* (2013.01); *A61J 3/074* (2013.01); *G06F 19/00* (2013.01);
(Continued)

(58) Field of Classification Search
None
See application file for complete search history.

(56) References Cited

U.S. PATENT DOCUMENTS

| 4,983,401 A * | 1/1991 | Eichel ............... A61K 9/5042 424/458 |
| 5,699,649 A | 12/1997 | Abrams et al. ............ 53/428 |

(Continued)

FOREIGN PATENT DOCUMENTS

| JP | 5-502529 | 4/1993 | ............. G06F 15/21 |
| JP | 2004-534571 | 11/2004 | ................ A61J 7/00 |

(Continued)

OTHER PUBLICATIONS

International Preliminary Report on Patentability issued in corresponding application No. PCT/US2011/047809, dated Feb. 19, 2013 (10 pgs).

(Continued)

*Primary Examiner* — Jonathan Ng
*Assistant Examiner* — William G Lultschik
(74) *Attorney, Agent, or Firm* — Hayes Soloway PC

(57) ABSTRACT

A system and method for determining an optimal combination drug product for a particular patient includes a processor that receives patient information and determines an optimal combination drug product based on the received information. A system which can provide information regarding predicted events or pathologies based on received patient information and guidance on subsequent steps to ameliorate, treat or intervent. A drug production device includes a plurality of drug containers, each of which are coupled to a drug dispensing channel. A controller controls the dispensing of drug through each channel, and a combination drug product is produced from the dispensed drugs. A combination drug product includes a plurality of discrete units of a first drug, and a plurality of discrete units of a second drug. A transdermal patch includes a plurality of drug compartments, each containing a quantity of drug product, and a controller for controlling the release of drugs from each compartment. Feedback loop elements can enable iterations to optimized personalized doses.

36 Claims, 9 Drawing Sheets

(51) Int. Cl.
*G06F 7/00* (2006.01)
*B65D 41/00* (2006.01)
*A61J 3/07* (2006.01)
*B65D 51/28* (2006.01)
*G06F 19/00* (2018.01)
*G06Q 50/22* (2018.01)
*A61J 1/03* (2006.01)

(52) U.S. Cl.
CPC ......... *G06F 19/3456* (2013.01); *G06Q 50/22* (2013.01); *A61J 1/03* (2013.01); *A61J 2200/30* (2013.01); *A61J 2205/60* (2013.01); *A61M 35/00* (2013.01); *A61M 2205/52* (2013.01); *A61M 2205/6009* (2013.01); *A61M 2205/6054* (2013.01); *Y02A 90/22* (2018.01); *Y02A 90/26* (2018.01)

(56) References Cited

U.S. PATENT DOCUMENTS

| | | | | |
|---|---|---|---|---|
| 5,941,380 | A * | 8/1999 | Rothman | 206/222 |
| 5,960,609 | A | 10/1999 | Abrams et al. | 53/428 |
| 6,428,809 | B1 | 8/2002 | Abrams et al. | 424/451 |
| 6,510,430 | B1 * | 1/2003 | Oberwager | G06F 19/3418 128/921 |
| 6,564,121 | B1 * | 5/2003 | Wallace et al. | 700/231 |
| 6,658,396 | B1 | 12/2003 | Tang et al. | 706/17 |
| 6,702,683 | B2 | 3/2004 | Abrams et al. | 464/465 |
| 6,923,979 | B2 | 8/2005 | Fotland et al. | 424/439 |
| 7,080,755 | B2 | 7/2006 | Handfield | 221/13 |
| 7,404,968 | B2 | 7/2008 | Abrams et al. | 424/443 |
| 8,116,907 | B2 | 2/2012 | Hyde | 700/236 |
| 8,718,817 | B2 * | 5/2014 | Hyde et al. | 700/231 |
| 2002/0042725 | A1 * | 4/2002 | Mayaud | 705/2 |
| 2003/0010791 | A1 * | 1/2003 | Gentiluomo | A61J 3/002 221/92 |
| 2004/0158350 | A1 | 8/2004 | Ostergaard et al. | 700/231 |
| 2004/0172169 | A1 * | 9/2004 | Wright, IV | A61J 3/074 700/265 |
| 2005/0086008 | A1 * | 4/2005 | DiGianfilippo | A61J 3/002 702/19 |
| 2005/0150488 | A1 | 7/2005 | Dave | A61M 11/00 |
| 2005/0210834 | A1 * | 9/2005 | Kamineni | A61J 1/20 53/415 |
| 2006/0089856 | A1 * | 4/2006 | Kadhiresan et al. | 705/2 |
| 2007/0016443 | A1 | 1/2007 | Wachman et al. | 705/2 |
| 2007/0087048 | A1 | 4/2007 | Abrams et al. | 424/451 |
| 2007/0122824 | A1 * | 5/2007 | Tucker et al. | 435/6 |
| 2007/0186923 | A1 | 8/2007 | Poutiatine | A61J 7/0038 |
| 2008/0131362 | A1 * | 6/2008 | Rousso | A61B 5/417 424/1.11 |
| 2008/0195249 | A1 | 8/2008 | Rousso et al. | 700/231 |
| 2009/0025741 | A1 | 1/2009 | Crawford et al. | 131/359 |
| 2009/0057328 | A1 | 3/2009 | Ratnakar | 221/1 |
| 2009/0105876 | A1 | 4/2009 | Simpson et al. | 700/242 |
| 2010/0100391 | A1 * | 4/2010 | Daya et al. | 705/2 |
| 2010/0131097 | A1 * | 5/2010 | Young | G01N 21/31 700/244 |
| 2010/0270257 | A1 | 10/2010 | Wachman et al. | 215/228 |
| 2010/0324728 | A1 | 12/2010 | Rosenblum | 700/242 |
| 2011/0146835 | A1 * | 6/2011 | Terzini | 141/1 |
| 2012/0189693 | A1 * | 7/2012 | Dick | A61J 3/10 424/465 |
| 2012/0232473 | A1 | 9/2012 | Poutiatine | 604/60 |

FOREIGN PATENT DOCUMENTS

| | | | | |
|---|---|---|---|---|
| JP | 2005-517504 | 6/2005 | ............ | A61M 15/00 |
| JP | 2007522036 | 8/2007 | ............ | B65D 51/28 |
| JP | 2008-510588 | 10/2008 | ............ | A61J 7/00 |
| JP | 2010-170504 | 8/2010 | ............ | G06Q 50/00 |
| WO | WO 91/05310 | 4/1991 | ............ | G06F 15/42 |
| WO | WO 9961324 | 12/1999 | | |
| WO | WO 2002/069897 | 12/2002 | | |
| WO | WO2005073103 | 8/2005 | ............ | B65D 51/28 |
| WO | WO 2006/028944 | 3/2006 | | |
| WO | WO2012021899 | 2/2012 | ............ | G06Q 50/00 |

OTHER PUBLICATIONS

PCT International Search Report and the Written Opinion, dated Mar. 16, 2012 (15 pgs).
Mexico Office Action, Appln. No. mx/A/2013/001744, with English translation; dated Jan. 30, 2014 (6 pgs).
Mexico Office Action, Appln. No. MX/a/2013/001744, with English translation; dated Jun. 20, 2014 (5 pgs).
Australian Office Action issued in related Australian Patent Appln. Serial No. 2011289158 dated Jun. 19, 2014 (4 pgs).
Mexican Office Action issued in corresponding Mexican Patent Appln. Serial No. MX/a/2013/001744 dated Apr. 10, 2014, with English translation (5 pgs).
Japanese Official Action issued in related Japanese Patent Appln. Serial No. 2013-524264, dated Jul. 7, 2015 with translation (9 pgs).
Chinese Office Action (w/translation) issued in application No. 201180049177.5, dated Aug. 19, 2015 (18 pgs).
International Search Report and Written Opinion issued in related PCT Patent Appln. Serial No. PCT/US12/52551 dated Nov. 2, 2012 (11 pgs).
Extended European Search Report issued in related EPO Patent Appln. No. 12827879.3-1651, dated Apr, 21, 2015 (7 pgs).
Office Action issued in corresponding Japanese Patent Appln. No. 2013-524264 dated Feb. 29, 2016 with English translation (6 pgs).
Office Action issued in corresponding Japanese Patent Appln. No. 2014-528500 dated Apr. 13, 2016 with English translation (15 pgs).
Office Action issued in corresponding European Patent Appln. No. 11817178.4, dated Apr. 18, 2016 (7 pgs).
Japanese Office Action issued in application No. 2014-528500, dated Sep. 15, 2016, with machine English translation (18 pgs).
Japanese Decision of Refusal issued in application No. 2013-524264, dated Feb. 29, 2016 (6 pgs).
Chinese Office Action issued in application No. 201180049177.5, dated Jul. 5, 2016 (21 pgs).
EP Office Action with Supplementary European Search Report, issued in EP application No. 11817178.4, dated Nov. 7, 2016 (17 pages).
Japanese Office Action (w/translation) issued in application No. 2016-135871 dated May 15, 2017 (9 pgs).
Chinese Office Action with translation, issued in Chinese application No. 201180049177.5, dated Feb. 22, 2017(25 pages).
Japanese Decision of Refusal dated Mar. 24, 2017 with translation issued in Japanese Patent Application Serial No. 2014-528500 (14 pages).
Office Action issued in U.S. Appl. No. 14/241,799, dated Oct. 6, 2017 (15 pgs).
Canadian Office Action issued in application No. 2,807,949, dated Jul. 17, 2018 (3 pgs).
Chinese Office Action (no translation) issued in application No. 201180049177.5, dated Mar. 29, 2018 (10 pgs).
European Office Action issued in application No. 12 827 879.3, dated Mar. 8, 2018 (4 pgs).
Japanese Office Action (w/translation) issued in application No. 2016-135871, dated Mar. 28, 2018 (6 pgs).
Office Action issued in U.S. Appl. No. 14/241,799, dated Apr. 20, 2018 (13 pgs).

* cited by examiner

SYSTEM AND METHODS FOR THE PRODUCTION OF PERSONALIZED DRUG PRODUCTS

CROSS REFERENCE TO RELATED APPLICATION

This application claims priority from U.S. Provisional Application Ser. No. 61/401,503, filed Aug. 13, 2010, the contents of which are incorporated herein by reference.

FIELD

The present invention relates to systems, method, and devices for recommending or medicating an optimal treatment protocol and/or an optimal drug selection, combination and dosage for a particular patient, in particular, by utilizing patient information in combination with available medical and other relevant information and datasets to determine, predict or suggest an optimal drug or therapy. The present invention further relates to combination drug products, to systems, i.e. methods and devices for delivering combination drug products, and to devices for holding a quantity of drug that is used within a drug production device. The invention has particular utility for producing personalized drug products, and will be described in connection with such utility, although other utilities are contemplated.

BACKGROUND

Individual patients have unique needs for medication and therapeutics, whether that might be for general wellness (e.g., vitamins or other supplements, or preventative drugs based on individualized risk factors from, for example, known environmental and genetic factors), for prevention or prophylactic purposes, or for the treatment of single or multiple acute and/or often complex and sometimes chronic disease pathologies.

The standard of care in medicine is to treat patients with various drugs, most often in pill/tablet form as an outpatient. This can often lead to a high "pill burden" and is sometimes termed polypharmacy. Poor compliance often follows. Poor adherence to medication and prescribed health of medical related regimens is a recognized medical problem in the U.S. and abroad. At least a third of all medication-related hospital admissions are caused by poor medication adherence, and these events alone are estimated to cost $100 billion annually in the USA. (PMID 18183470, *J Gen Intern Med.* 2008 February; 23(2):216-8. Medication Adherence After Myocardial Infarction: A Long Way Left To Go. Choudhry N K, Winkelmayer W C.) Many studies demonstrate that chronic illnesses like diabetes, hypertension, heart disease, or ulcerative colitis worsen when patients fail to take medications as prescribed—and this puts additional burdens not only on individuals, but the health care system. Additionally preventative regimens, such as taking of a statin to lower high cholesterol levels can lead to prevention of coronary artery disease, as well as the resulting disease morbidity and related costs.

For example, an adult patient with hypertension and a history of coronary artery disease (CAD) and a prior heart attack/myocardial infarction might commonly be prescribed "standard" doses of low dose (81 mg) aspirin, a cholesterol lowering medication, a beta-blocker, an ACE inhibitor, and a diuretic such as hydrochlorothiazide. Additional prescribed drugs might include digoxin, a multivitamin, and medication for blood glucose control to help manage co-morbidities such as type II diabetes.

Multiple medication prescriptions (or polypharmacy) have been shown to dramatically lower patient compliance. See, e.g., van Bruggen, R. "Refill adherence and polypharmacy among patients with type 2 diabetes in general practice." *Pharmacoepidemiol and Drug Safety.* 18.11 (2009): 983-91. Many older patients are faced with up to a dozen or sometimes more separate prescribed medications ranging from pills to eye drops, requiring complex regimens, sorting and scheduling. Patient and family/caregiver education about the problems being treated or prevented, and understanding the prescribing clinicians instructions on the dosing, timing is also often non-optimal given the limitations of clinician and medical staff time-even when the basic prescribing information is on the pill bottle, many patients are not clear on what the mediation is for, or how to best take it or when not to take it, for example to 'hold' an antihypertensive when blood pressures are running low. These issues, and others can lead to poor adherence/compliance, mix-ups, underdosing and overdoses, and therefore clinical outcome suffers, leading to further disease progression, pathology, clinical needs, hospitalizations, increased healthcare costs, as well as increased morbidity and mortality. It has been estimated that 10% of hospital admissions are related to medication errors and problems with compliance.

Pharmacogenomics refers to the entire spectrum of genes that determine drug behavior and sensitivity, whereas pharmacogenetics is often used to define the narrower spectrum of inherited differences in drug metabolism and disposition. The benefits of pharmacogenomics are numerous. For example, prescribing clinicians, as well as pharmaceutical companies could exclude those people who are known to have a negative response to the drug, based upon clinical trials and potentially on correlation of side effects or other issues which correlate to one or more genes or gene variant (as determined by Single Nucleotide Polymorphism (SNP) analysis (which is available and common today) to sequencing (becoming lower cost and more common)). This, of course, increases the probability that the drug might be a success with a particular population. Pharmacogenetic and ever cheaper and more available genotyping will identify many new disease-related genes and provide an explosion of new targets to pursue; and pharmacogenomics profiling (with or without additional patient specific information) will lead to patient stratification, and these new targets, as well as existing targets, will be divided into subsets. It has been estimated that genotyping will identify new disease related genes that will lead to between 5,000 and 10,000 new potential targets. Because the current amount of targets is approximately 500 and is comprised of mainly four target classes, such as G-protein-coupled receptors ion channels, nuclear hormone receptors and enzymes, these new targets will add genomic and medicinal diversity. The FDA already has many approved drugs with pharmacogenomic information in their labels. See http://www.fda.gov/drugs/sciencere-search/researchareas/pharmacogenetics/uc083378.htm. And queriable databases have been compiled and continue to be expanded as new research is published, which contain various drugs and specific genes which affect them, for example the PharmGkb database (http://www.pharmgk-b.org)

Some drugs are metabolized by several pharmacologic polymorphic genes (including, for example, the CYP (cytochrome P450) family of liver enzymes responsible for breaking down over 30 different classes of drugs), and other drugs (and/or dietary intake of various vitamins or other compounds) can inhibit or induce these same enzymatic and other genes/proteins. For example, Vitamin K intake (which may be provided from a diet including leafy green vegetables) can interact with warfarin (Coumadin), and components in grapefruit can interfere with several kinds of prescription medications. These combinations and their various effects should be considered when prescribing medications, but often are not known (genetics of patient aren't known) and/or not presented to the prescribing clinician, and the impact of various patient attributes (ranging from weight, to renal function) on various multi-drug effects not determined or calculated. This can lead to drug toxicity, and drug overdoses, and contribute to many of the drug related side effects, complications, morbidity and deaths which occur in the US and rest of world each year.

Additionally some drugs, based on a patient's individual attributes, may be relatively or absolutely not indicated based on genetics, history of allergic reactions, or other factors. For example, many patients are prescribed aspirin to decrease risk of cardiovascular events including heart attack and stroke. However, recent scientific published studies have indicated that individuals who do not carry the LPA gene do not show significant risk reduction from taking daily aspirin. A clinician, aware of such information, may therefore choose not to prescribe aspirin (which has known side effects and risk including gastritis and increased risk of gastrointestinal bleeding) for those patients who are not LPA carriers.

In addition to drug dosing, the selection of drug is often important and can be informed by many attributes, ranging from genes, to age, renal function etc. One example is selection of statin for a particular patient based on genes. SLCO1B1, for example, is a key gene that affects both the metabolism and side effect profile of many statins. Understanding of the pharmacogenomics of genes related to statins, can for example help determine and guide a clinician as to whether a patient is likely to benefit, which statin to choose from and which dose. Similarly for selection, combination and dosings of various medications to treat hypertension, and other acute and chronic diseases.

While medications have general doses, these often are not ideal, as they do not account for side-effects, and a patients individual characteristics (which can affect drug selection and dosing), which range from but are not limited to weight, body surface area (BSA), body mass index (BMI) or Quetelet Index, lean body mass, percentage of body fat, kidney/renal function, metabolism of different drugs based on the patient's genetics (i.e. for liver enzymes which metabolize many drugs), and known or predicted drug-drug interactions. Additional patient-specific attributes which may influence how a particular patient will respond to a given drug include degree of physical activity, exercise, diet (for example, amount of Vitamin-K in consumption of leafy green vegetables can dramatically effect dosing requirements for Coumadin), habits (including smoking and alcohol consumption), social network data, spending information.

Manufactured pill/tablet drugs however are usually "one size fits all" and are typically produced in a limited number of approved forms/dosages, and therefore in many cases under-dose the patient, and in others can lead to overdoses and other toxicities.

While individual drugs may be prescribed, as the ability of biomedical technology to achieve "personalized medicine" (i.e. the right drug(s), at the right dose, for the right person at the right time) based on genetics and other factors is becoming possible, however polypharmacy (multiple drugs prescribed), if integrated into combination dosing would greatly enhance ease of therapy, compliance (also termed 'adherence') and efficacy, and would translate to better prevention/prophylaxis, improved outcomes, decreased disease, suffering and lower healthcare costs.

Compounding (i.e. pharmaceutical compounding and compounding pharmacy) is the mixing (and in some cases reformulation) of drugs by a pharmacist, physician, or veterinarian to fit the unique needs of a patient. This may be done for medically necessary reasons, such as to change the form of the medication from a solid pill to a liquid, to avoid a non-essential ingredient that the patient is allergic to, or to obtain the exact dose needed or prescribed of one or more medications. It may also be done for voluntary reasons, such as adding favorite flavors to a medication. It is generally done manually by the pharmacist, is time consuming and expensive. In current standard use, compounding pharmacists can prepare and combine one or more medications using several unique delivery systems, such as a sublingual troche or lozenge, a lollipop, capsule, or a transdermal gel or cream that can be absorbed through the skin. For those patients who are having a hard time swallowing a capsule, a compounding pharmacist can make a liquid suspension instead.

In addition, clinical trials, and the safety, efficacy measures required to develop new drugs and combinations often requires extensive, rigorous and expensive and phased clinical trials. Assurance that trial subjects are actually taking the test drugs/placebo or other medical components is critical to accurate assessment. Better means of tracking compliance during clinical trials will lead to safer, more effective drugs entering the market.

Feedback from patient to clinician is often very limited, in terms of both the impact and benefits and the side effects of one or drugs on treating the patient (includes treatment, prophylaxis, etc). Improved feedback mechanisms could enable 'tuning' or changing of medications to faster, more time efficient and convenient means to achieve optimal dosing, improved outcomes, minimized side effects and improved compliance. Feedback can consist of (but not be limited to) physiologic data (i.e. vital signs (blood pressure, pulse, temperature) blood chemistries (i.e. blood glucose), subjective measures (energy, mood) etc. For example a patient may be newly diagnosed with hypertension and prescribed in an informed or empiric manner one or more medications designed to lower blood pressure. As is common in medical practice today, the patient may or may not measure blood pressure values in the home or other environment, and the resulting information as to whether the medications(s) were effective is limited or lacking, and other factors which could be influencing blood pressure (including time of day, activity, diet) are not determined. Feedback mechanisms, by which the blood pressure (BP) values can be measured (for example with mobile BP measuring system which is connected via smart phone to the web and the patient record), could enable the patient, other caregivers and clinician to have insight into the effects of their medicine and impact of other factors (i.e. sleep, salt intake). By providing means for the measures from the blood pressures to be provided back to the clinicians, or a 'intelligent system with pre-determined algorithms, rules, or decision tree type structures to then help the patient of physician decide whether a particular medication needs to be stopped, adjusted, or added to. Such a system could save time in the iteration of drug dosing and combinations, and lead to better outcomes, adherence, and cost savings.

SUMMARY

The present disclosure is directed to systems, methods and devices that overcome the aforesaid and other disadvantages of the prior art. Briefly described, the present disclosure provides a system and method for the production and delivery of a personalized drug product.

In one aspect, the present disclosure provides a system for producing a drug product for an individual patient that includes a computer processor that is configured to receive information relating to the patient and to predict, based on the received patient information, an optimal drug selection, combination and dosage for the patient. The system further includes a drug production device, in communication with the processor, which produces the drug product based on the predicted optimal drug selection, combination and dosage.

In another aspect, the present disclosure provides a drug production device that includes a plurality of drug containers, each configured to hold a quantity of a drug; a plurality of drug dispensers, each of the drug dispensers coupled to one of the drug containers; and a controller, which controls the dispensing of drug by each dispenser. A combination drug product is produced from the dispensed drugs.

In yet another aspect, the present disclosure provides a bottle cap for containing one or more drugs, the cap being configured to fit onto a bottle, said cap containing one or more drugs within a space formed between a frangible seal and under the cap, wherein, in use, said frangible seal is configured to be punctured or otherwise opened upon activating the cap whereby to empty drugs contained under the cap into liquid contained in the bottle.

In still another aspect, the present disclosure provides a cartridge for holding a bulk quantity of drug. The cartridge includes a unique coupling element, and the coupling element is configured to couple to a drug formulation device having an element to accommodate the coupling element of the drug cartridge. The unique coupling element may include unique machine readable indicia for identifying the drug contained within the cartridge.

In another aspect, the present disclosure provides a method of predicting an optimal combination drug product for a particular patient, which includes: receiving, by a processor, information relating to the patient and other relevant information, ranging from, for example, pharmacognomics, weather, CDC and other information sources that are not unique to the patient; and predicting, by the processor, an optimal drug selection, combination and dosage and other aspects of a preventative or therapeutic regimen including timing of taking a drug, tapering and layering of different drugs and other modalities for the particular patient, based on the received information.

In yet a further aspect, the present disclosure provides a non-transitory computer readable medium encoding a computer program for predicting an optimal combination drug product for an individual patient, which includes first program instructions usable on a processor, for receiving information relating to the patient and other relevant information, and for predicting, by the processor, an optimal drug selection, combination and dosage for the particular patient, based on said received patient information.

In another aspect, the present disclosure provides a combination drug product including a plurality of discrete units of a first drug, and a plurality of discrete units of a second drug.

In still a further aspect, the present disclosure provides a method of predicting an optimal treatment protocol for an individual patient, that includes: receiving, by a processor, information relating to the patient; and predicting, by the processor, an optimal treatment protocol for the particular patient, based on said received patient information.

In yet another aspect, the present disclosure provides a patch for transdermal delivery of a drug product that includes a plurality of drug compartments, each containing a quantity of drug product, and a controller for controlling the release of drugs from each of said drug compartments.

In still yet another aspect, the present disclosure permits a clinician/prescriber to transmit information about drugs/doses, etc., in a personalized pill, along with other standard medications which might be prescribed in conjunction, or of standard medications alone, for example, a proprietary/non generic pill. This information and timing information is transmitted to the patient electronically, thru cloud, web/wifi, etc., to device such as mobile phone or tablet, or bedside or bathroom sink display or device to include 'When' to take the personalized and other med, and how, e.g., with food, such that compliance, adherence reminders are provided to the patient and/or caregivers.

The device/system can contain educational material such as 'why', for example, information on a statin, specifics about the drug, its class of medications, its possible benefits and risks, and also about the condition (high cholesterol) for which the patient is being treated. This educational information could include embedded or linked videos/animations, weblinks, text, audio or any other form of information, including educational 'games' with which to become familiar with the medicine and to potentially enhance compliance, feedback.

This enabled tracking of compliance/adherence, and feedback on adherence to the patient and caregivers, optionally in real time, i.e. a patient's mother, in the case of a child, is texted or otherwise informed when patient has taken, or has missed a dose or multiple doses. This tracking can be done via manual entry of 'dose taken' i.e. via a mobile device, a phone app or via any number of medical dispensers (including dispensers which communicate with the application or via the cloud or other system, and that can dispense based on the feedback and elements described in this application, appropriate drugs and doses, both in pill, liquid (i.e. ophthalmic drop), patch or other form of dispensation). The 'app' on the patient's device or devices can allow integration of wearable/external device information (i.e. vital signs or blood glucose) and also input and recording of subjective symptoms and side effects. This enables feedback further to inform future individualized of personalized medications or of standard drug regimen dosing.

In yet another aspect of the present disclosure, the clinician may elect to do programmed/iterative 'smart prescription' as opposed to emperic or primary dosing recommendations. This enables the clinician to prescribe, for example, a low dose of a blood pressure agent (such as beta blocker) and to follow actual blood pressure measures, and based on the BP results, iterate on the next version of a personalized pill or standard pills. This iteration can be optionally done 'autonomously', based upon the prior instructions/guidelines/protocols embedded/prescribed. For example, if evening BPs are running above targets an evening dose of the beta blocker or additional anti-hypertensive could be added to the regimen, for individual (i.e. standard medicine (tablets or otherwise) either at that same time the pill is manufactured on site, or on next versions shipped or sent from central or local pharmacy. Also, subject symptoms or reactions, e.g.

changes in energy level, headaches, weight gain or weight loss, irritability, frequency or other subjective symptoms or reactions also may be employed in generating a smart prescription.

The prescription and instructions and related decision-tree type rule based algorithms can be selected (i.e. from a template of decision tree or otherwise pre-existing algorithms, decision trees, protocols etc), modified, or fully authored by the providing clinician. Such an embodiment enables partially to fully autonomous modification of dosings/drug combinations selection and combination personalized pill production.

In another aspect, the information obtained regarding the patient (their personal attributes, and data), as described for the optimization, prediction and recommendation of personalized and preventative and therapeutic interventions can be utilized to provide an 'early warning system'. In this way signals and trends (both acute and occurring over longer periods of time (days to months) such as a change of weight, change in behaviors (e.g. increased cough, changes in sleep), alterations in various activity levels, and a change or measurable signs in various physiologic measures (measured for example from body fluids, internal or external monitors etc) could provide a 'flag' for the patient to obtain medical evaluation (e.g. early signs of malignancy (which might include weight loss, changes in biomarkers), or other pending acute events (stroke, myocardial infarction) which the system, by various means, potentially including databases, predictive algorithms, Artificial enhanced analytics and other means available show a significant heightened likelihood based on the patients attributes and information of an acute event, or signs of early disease (cancer, infection, or other pathologies). The system which as described in this disclosure which are used to suggest therapy modalities can similarly inform the patient and or caregiver, clinical provider or healthcare system that medical evaluation is likely needed. An analogy between automobile systems (such as the "Onstar" system by General Motors) which monitors various automobile sensors and can activate the 'check engine' light indicating that service is needed. Also such a medical system can inform the healthcare provider, family, 911 emergency services etc, if an acute or emergency event has occurred, and activate various responses, ranging from EMS/Ambulance, to data provided to the patient via the system as to appropriate interventions, ranging from where to find the closest emergency room, to particular therapeutics (drug or otherwise) to utilize depending on the situation. As an example, multiple modalities regarding an individual are monitored over time, and based on the patients attributes (age, sex, genetics, exposures etc) warnings can be made via various predictive analytics (and set to various levels of sensitivities (e.g. 10% versus 25% or 75% likelihood of having a particular acute event or new diagnosis). This could be useful for example in an individual patient who is a long time smoker. The incorporated information notes a slow decline in weight, with a detection via mobile phone that the patient has been coughing at a higher level than baseline, and that there has been a detectable change in baseline respiratory rate. Blood biomarkers, oxygen saturation or other values may be examined by the system, and based on information, suggest that the patient be evaluated for potential pulmonary pathology (e.g. early detection of a lung cancer). Such a system may enable subtle changes to lead to much earlier diagnosis (e.g. Stage I cancer), as opposed to more advanced stage as more commonly occurs for patients diagnosed with lung or other malignancies. Similarly symptoms of low grade fevers, combined with travel history, and various measures of blood parameters, vital signs etc, may suggest symptoms of malaria, and prompt a medical evaluation and workup which may have otherwise been delayed until symptoms were more evident or persistent. Similarly various heart arythmias, detected by external or implanted devices could be monitored frequently, and in conjunction with patient known attributes including genetics and behavior, and possibly from 'crowd sourced' information obtained from large patient data sets and monitoring) indicated that a patient was at very high risk for having a complete coronary occlusion and subsequent myocardial infarction. The system, by various means, including text, mobile phone application, or other modalities, can inform the patient, their family/caregivers, their clinician or caregiver team, that a clinical event was imminent or a new diagnosis (e.g. diabetes, influenza or any pathology). This would give the patient means (and personal information provided as to where to followup depending on the clinical urgency) for further evaluation (which could include directions to a medical facility), treatment guidance (e.g. aspirin for an individual who was exhibiting signs of pending myocardial infarction)

The features, functions, and advantages that have been discussed can be achieved independently in various embodiments of the present disclosure or may be combined in yet other embodiments further details of which can be seen with reference to the following description and drawings.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further features and advantages of the invention will be seen from the following detailed description, taken in conjunction with the accompanying drawings, wherein like numerals depict like parts, and wherein.

DETAILED DESCRIPTION

Figure 1:
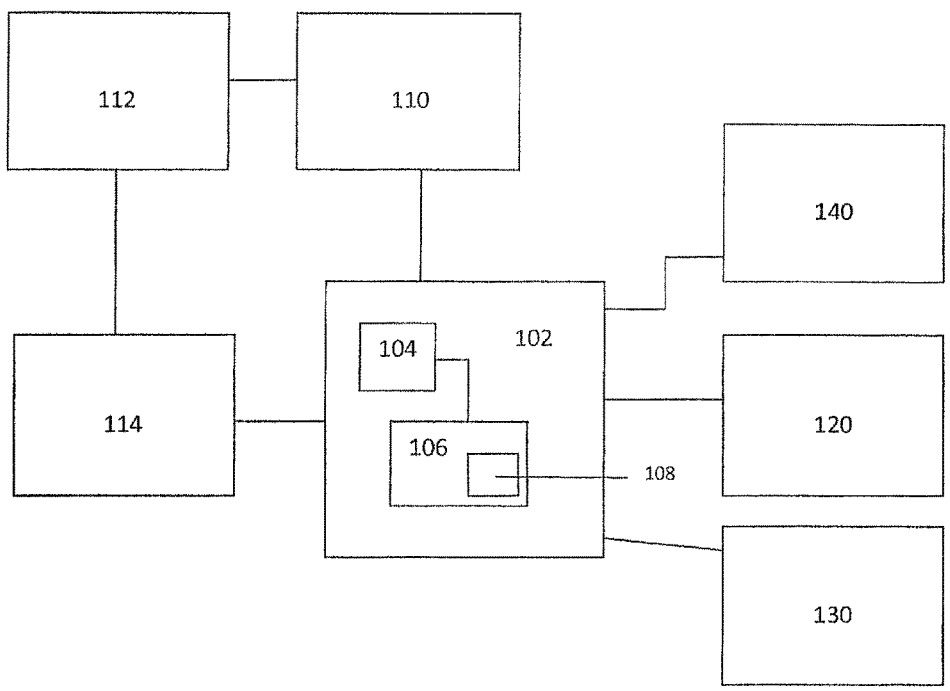
FIG. 1 is an illustration of a block diagram of a system for predicting an optimal combination drug product for a particular patient, in accordance with an embodiment of the present disclosure.

As used herein the term "predict" or "predicting" is intended to include providing intelligent, evidence based guidance to determine, recommend, guide, suggest or select a treatment protocol such as an optimal drug combination and dosage for a particular patient, i.e. a personalized drug treatment or treatment protocol. The term "predict" also may include an optimal drug selection, combination and dosage, utilizing patient feedback information or reference information, i.e. the system may "learn" such that future predictions may become successively more accurate and tailored to the patient, or other patients.

Also, the term "patient" may include both a human patient, and a non-human animal patient.

The term "drug", as used throughout this disclosure, includes pharmaceutical medicines, nutriceuticals, supplements, vitamins, minerals, nutraceuticals and the like, in any form. A "drug" may be used for treatment/therapy of acute or chronic disease, for prophylaxis and disease prevention, as well as for enhancing health, longevity and general "wellness."

While the following description generally refers, in parts, to an optimal drug selection, combination and/or dosage, one having ordinary skill will readily understand that the present invention may advantageously be employed to predict and/or suggest an optimal treatment protocol and/or combination of treatments. By way of example, without limitation, a treatment protocol may include a particular diet or exercise regimen, a suggested physical therapy program, a suggested implant, device or a suggested medical procedure, operation or surgery or drug or drugs.

Furthermore, the present disclosure refers to a drug selection, combination and dosage. One having ordinary skill will readily understand that "dosage" refers not only to the dosage of an entire combination drug product, but also to the dosages of each component drug which makes up a combination drug product.

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

Many embodiments of the invention may take the form of computer-executable instructions, including elements of an Inference Engine (http://en.wikipedia.org/wiki/Inference_engine), with algorithms executed by a programmable computer. Those skilled in the relevant art will appreciate that the invention can be practiced with other computer system configurations as well. Certain aspects of the invention can be embodied in a special-purpose computer or data processor that is specifically programmed, configured or constructed to perform one or more of the computer-executable algorithms described below. Accordingly, the term "computer" as generally used herein refers to any data processor and includes Internet appliances, hand-held devices, palm-top computers, wearable computers, cellular or mobile phones, multi-processor systems, processor-based or programmable consumer electronics, network computers, minicomputers and the like.

The invention can also be practiced in distributed computing environments, where tasks or modules are performed by remote processing devices that are linked through a communications network. Moreover, the invention can be practiced in Internet-based or cloud computing environments, where shared resources, software and information may be provided to computers and other devices on demand. In a distributed computing environment, program modules or subroutines may be located in both local and remote memory storage devices. Aspects of the invention described below may be stored or distributed on computer-readable media, including magnetic and optically readable and removable computer disks, fixed magnetic disks, floppy disk drive, optical disk drive, magneto-optical disk drive, magnetic tape, hard-disk drive (HDD), solid state drive (SSD), compact flash or non-volatile memory, as well as distributed electronically over networks. Data structures and transmissions of data particular to aspects of the invention are also encompassed within the scope of the invention. Communication between devices or components provided herein may be accomplished over any wired or wireless network that enables communication between devices, including local area networks (LAN), wide area networks (WAN), the Internet, Wireless LAN, Wi-Fi, mobile device networks, IEEE 802.11, GSM, GPRS, UMTS, WMAN, BWA (LMDS, WiMAX, AIDAAS and HiperMAN), 3G and 4 G communications protocols, Bluetooth, or any other network arrangement and/or protocol known to those having ordinary skill in the relevant art.

FIG. 1 illustrates a system for predicting an optimal combination drug product for a particular patient, in accordance with a first exemplary embodiment of the disclosure. A computer 102 receives patient information 110 specific to a particular person. The computer 102 may include a processor 104 and computer-readable memory 106. The patient information 110 may include any physiological or general health information for a specific person, as well as information for particular drugs. The patient information 110 may include, by way of example, without limitation, information relating to a person's: weight; height; age; sex; body mass index; metabolism; renal function; blood chemistries, biomarkers, liver enzymes; proteomics, expression profiling, imaging data (i.e. from CT/MRI/Ultrasound), pharmacokinetics; risk factors for disease; current medications; other medications; history of prior side effects to one or more medications; partial or full genome SNP screening data; analysis of pharmacogenomic/pharmacogenetic profile; known and calculated/predicted drug-drug interactions and drug-diet or other known interactions; whole or partial genome analysis; vitamin deficiencies; diet; drug allergies and/or sensitivities; environmental, toxin or other allergy history; the patient's medical history, diagnostic information; exercise activity; sleep activities; tissue expression profiling hormonal cycles, biomarker information, behavioral history, geographic history, including exposures or potential exposures to toxins and other environmental factors (including exposure to radiation, etc.), compliance history, radiologic/imaging information, demographic information; patient's medical history; diagnostic information; exercise activity; monthly reproductive cycle; sleep activities; tissue expression profiling, geolocation, social network, consumer information, habits, physiologic data, EEG information, behavioral history, geographic history, exposures or potential exposures to toxins and other environmental factors including exposure to radiation, compliance history and personality testing from body measurement devices, and/or personality testing (i.e. Myers Brigs or other psychological evaluation or test). Such a system and the information obtained over time (e.g. trends and changes) can be utilized with predictive modeling as an early warning system by which to inform the patient and or caregivers, clinician and other providers information which may enable early diagnosis of various pathologies, potentially at earlier stages than normally diagnosed (e.g. malignancy, infection, diabetes, and other medical conditions).

Information can then be delivered to the individual patient/caregiver as to suggested interventions (e.g. directions to emergency rooms, or to take an aspirin in the setting of a likely imminent myocardial infarction).

The patient information 110 may further include information about the person's exercise activity (for example, as measured by a pedometer), monthly reproductive cycle (in women), general activity to include sleep habits and sleep tracking (e.g., time in various stages of sleep), physiologic data to include various discrete, regularly or continuously measured (for example but not limited to vital signs (e.g., heart rates, respiration, temperature, blood pressures, brain recording (e.g. EEG signals)) and laboratory elements (e.g., blood sugars, hormone levels, proteomic and biomarker data). The patient information 110 may further include information received from a social network and/or credit card, gym activity, and spending activity. Such information, for example, may be received from devices, computers, servers, etc. which may communicate with the computer 102 over any network.

The biomarker information may include, by way of example, without limitation, information from proteins, carbohydrates, amino acids and other chemicals and molecules as measured singly or in conjunction with one or more in any way from the blood, urine, sweat, saliva or other body tissue, biopsy or bodily fluid.

The patient information 110 may further include, by way of example, without limitation, information relating to: demographics, place of residence, locality (e.g., manually input or directly acquired from GPS tracking via a GPS-enabled mobile phone, or any other GPS-enabled device, or any other known location-acquiring means), occupation, environmental exposures (which may be informed by location history), medical history, diagnostics, rules based and evidence based medicine, tissue expression profiling, radiologic imaging data, and proteomics.

The patient information 110 may further include, by way of example, without limitation, information regarding the patient's prior medical and family medical history and/or disease conditions, current medications and all available medications, supplements, and diet. Furthermore, the patient information 110 may include information stored in a patient's electronic medical record (EMR) or patient health record (PHR).

The patient information 110 may be manually input into the system 100 via an input/output ("I/O") interface, which may include a keyboard, touchscreen or any other known I/O interface including by dictation and speech recognition. The patient information 110 also may be directly measured and automatically input into the computer 102. The computer 102 may receive patient information 110 from external measurement devices 112, which measure some category of patient information 110. For example, the computer 102 may receive information which is directly measured, by an external measurement device 112, from, for example, the patient's blood, urine, tissue and the like. The external measurement devices 112 may include implanted or temporarily implanted devices and sensors such as blood glucose monitors, ingestible devices, permanent or transiently placed epidermal or implanted electronics, micro-robots, wireless pills (for example, intelligent pills ("iPill") which include wireless communication capabilities), and the like.

Based on the received patient information 110, the processor 104 predicts an optimal drug selection and combination for the specific patient, including a dosage amount of each component drug. The processor 104 may further receive and/or access reference information 114. The reference information 114 includes information that relates patient information to an optimal selection, combination and/or dosage of different drugs. The reference information 114 may include prior-received patient information 114 for a particular patient, including information received from external measurement devices 112.

The system 100 may further include one or more database(s) 108, which may be provided within the computer 102, e.g. in the computer-readable memory 106, or may be located elsewhere and accessible to the computer 102 (for example, the database 108 may be made up of information derived from a plurality of databases, or individual pieces of information, which are accessible to the computer 102 over any network or other known forms of computer communication). The database 108 may store the received patient information 110, and further may store reference information 114 that relates patient information to optimal selection, combination and/or dosages of different drugs. For example, the database 108 may include a table which stores reference information 114 relating patient information to optimal selection, combination and/or dosages of different drugs. When the computer 102 receives patient information 110 for a specific person, the received patient information 110 may be compared to the reference information 114 stored in the database 108 and an optimal (or estimated optimal) combination drug product may be predicted.

For example, the computer 102 may receive the following patient information 110 for a particular person, "Patient A": male; age 59; BMI of 20, Weight of 165, lean body mass of 124, and current medications of Coumadin, Atenolol (beta blocker) and Hydrochlorthiazide (diuretic) Patient A also is prescribed an over-the counter baby aspirin and also takes a generic antacid (Cimetidine) (for a total of 5 daily medicines). The computer 102 then may access reference information 114, which may be stored, for example, in a look-up table, combinatorial bioinformatics or other medical-clinical information system (collectively referred to as a look-up table) in database 108, for each of the categories of received patient information 110 and correlate the received patient information 110 with pre-stored reference information 114, in order to determine an optimal drug selection, combination and dosage for the patient. For example, the look-up table may have pre-stored reference information 114 regarding the drug-drug interaction effects of Coumadin, Atenolol, Hydrochlorthiazide, baby aspirin and Cimetidine. The look-up table, for example, may contain reference information 114 indicating that certain drugs, when combined or taken together, have an additive effect or a cancelling effect. Moreover, the look-up table may contain reference information 114 indicating that the optimal drug selection, combination and dosage of a particular drug depends, in part, on the patient's age, weight, sex, BMI, genetics, renal function, hepatic function and/or any of the other categories of patient information 110. In this case, the computer 102 may predict the optimal selection, combination and dosage of the prescribed drugs, in combination, for the 59 year old male patient with a BMI of 20 and a fast metabolic rate.

Similarly, the look-up table may include reference information 114 for any of the categories of patient information 110 listed herein, as well as for other patient information that may be useful in predicircle a drug dosage for a patient. For example, the look-up table may include reference information 114 regarding coagulation measurements (e.g., prothrombin time (PT) and/or partial thromboplastin time (PTT)) and SNP genetic profile or full genomic sequence information. Thus, the optimal dosage for Patient A may be predicted based on these factors, as well as the patient information discussed above.

In one embodiment, the categories of information stored in the look-up table may each be given a different weighted value. For example, drug-drug interaction information may have more relevance in predicting an optimal drug combination than does information about a person's height. Thus, the drug-drug interaction information may be assigned a greater "weight" than is assigned to "height" information, and the processor 104 will take this into account when predicting the optimal drug selection, combination and dosage.

The predicted optimal drug combination for a specific patient may be output from the computer 102 to a display 120. In such an embodiment, a treating professional (e.g. a physician, nurse-practitioner or other prescribing professional) may then view the predicted optimal drug selection, combination and dosage, and then may prescribe, approve, modify or otherwise alter the predicted optimal drug selection, combination and dosage for the patient. The practitioner may optionally look deeper into the source of patient information 110 and/or reference information 114 (e.g., the clinical guidelines, data sets, evidence, measured data, etc) that informed the predicted drug selection, dose and combination. The patient information 110 and/or reference information 114 upon which the predicted optimal drug selection, combination and dosage was based may be output to the display 120. For instance, if the processor 104 recommended changing the dose and selection of cholesterol lowering Statin from YYY to a predicted optimal drug of ZZZ based on the SLCO1B1 gene variants of that particular patient, the practitioner could access the genetic information (for example, as provided to the display 120), as well as reference information 114 which may include summaries or the complete primary documents and publications and other evidence which support the particular prediction. See for example specific SLCO1B1 Variants and Statin-Induced Myopathy-A Genomecircle Study (REF: *N Engl. J. Med.* 2008 Aug. 21; 359(8):789-99. Epub 2008 Jul. 23.

Other techniques for predicting an optimal drug selection, combination and dosage, based on received patient and other relevant information 110, may be employed with the present invention. These may include methods of Systems Biology and Systems Medicine. For example, known Artificial Intelligence (AI) systems, techniques and algorithms may be adapted and employed within the system and methods of the present invention to predict an optimal drug combination and dosage. This may be in the form of an Inference Engine. Similarly, known search and optimization methodologies, statistical learning methods, artificial neural networks and control logic systems, techniques and algorithms may be adapted and employed within the system and methods of the present invention to predict an optimal drug selection, combination and dosage U.S. Pat. No. 6,658,396 to Tang et al., the entirety of which is incorporated herein by reference, provides a neural network drug estimation, the principles of which may be utilized with the system of the present invention to predict an optimal drug selection, combination and dosage.

A wide and nearly limitless variety of reference information 114 (which may exist in any form, structured or unstructured), from a variety of different sources may be accessed and utilized by the computer 102, in conjunction with patient information 110, to predict an optimal drug selection, combination and dosage. The reference information 114 may exist in database form, may be downloaded and stored in database 106, and/or may exist as separate pieces of information which may be distributed and stored in separate locations across a network, such as the Internet. The reference information 114, for example, may include information relating to the weather (e.g., for asthmatics), pollen counts, Centers for Disease control (CDC) information, medical diagnostic and statistical information, pharmacogenomic databases, dose calculators, information from the Food and Drug Administration (FDA), and any other information which may affect a person's response to a drug. The processor 104 may thus access the patient information 110 and the reference information 114 and predict an optimal selection, combination and dosage of a drug product utilizing AI or other "intelligent" computer methods and algorithms. Furthermore, the reference information may include patient feedback information, which may be, for example, directly measured by the external measurement devices 112 (e.g., side effects information, physiological response, heart rate, blood pressure, blood sugars, measures of sleep duration and sleep quality, symptomatic relief (e.g., headaches), etc.). Patient information 110 may include subjective patient feedback data which is reported by the patient. For example, the patient information 110 may include patient-reported information relating to the severity of headaches, stomach pain, irritability, level of energy, mood, sleep quality, or any other reported symptoms or signs. The patient feedback information allows the AI or "intelligent" computer to "learn" and improve its predicted optimal drug selection, combination and dosage.

Furthermore, the predicted optimal drug selection, combination and dosage may be sent to the specific patient's electronic medical record (EMR) 130, or to an individual or a number of pharmacies or pharmacy databases 150 where it may be stored.

The patient information 110, external measurement devices 112, reference information 114, EMR 130 and/or databases 150 may communicate with the computer 102 utilizing any known communication protocols and over any known communication networks or systems. Moreover, the system 100 may utilize feedback from any of these sources of information (as well as network-accessible crowd sourced or otherwise population based information) to "learn" and to more accurately predict or suggest an optimal therapeutic intervention or protocol, drug selection, combination and dosage. For example, the EMR 130 may include information that indicates that many patients having a specific SNP also experience a high incidence of one or more side effects to a particular medication or combination of medications. In such a case, this information may be communicated to the computer 102. The computer 102 (including processor 104) may then "learn" based on this information, and thus may update database 108 and/or reference information 114 with the information received from EMR 130. In this manner, the processor 104 may further base the optimal predictions on the information in the EMR 130 (e.g., that patients having the specific SNP have a high incidence of side effects to the particular medication or combination of medications).

In another embodiment, the predicted optimal drug selection, combination and dosage may be output directly to a drug production device 140 which may then automatically produce the predicted optimal combination drug for the specific patient. The drug production device 140 may be located, for example, at a centralized drug production facility, local pharmacy, nursing home, patient's place of residence, or any other location. The computer 102 may be integrated into the drug production device 140, or may be located outside of the device 140, as shown in FIG. 1. The computer 102 may communicate with the drug production device 140 and/or the patient's electronic medical record 130 over any wired or wireless network that enables communication between devices, including local area networks (LAN), wide area networks (WAN), the Internet, Wireless LAN, Wi-Fi, mobile device networks, IEEE 802.11, GSM, GPRS UMTS, WMAN, BWA (LMDS, WiMAX, AIDAAS and HiperMAN), 3G and 4 G communications protocols, Bluetooth, or any other network arrangement and/or protocol known to those having ordinary skill in the relevant art. Furthermore, information communicated between modules, databases, devices and the like, as provided herein, may be encrypted and transmitted in a private and secure manner which fully complies with HIPPA or similar regional privacy guidelines, rules and requirements.

In another embodiment, the predicted optimal drug timing and dosage may be output directly to a drug dispensation device which may then automatically or via means to inform the patient, that a particular medicine (which is already contained within the dispenser (portable or non-portable) to release or dispense the desired drug(s) for the specific patient at the most appropriate time.

Figure 2:
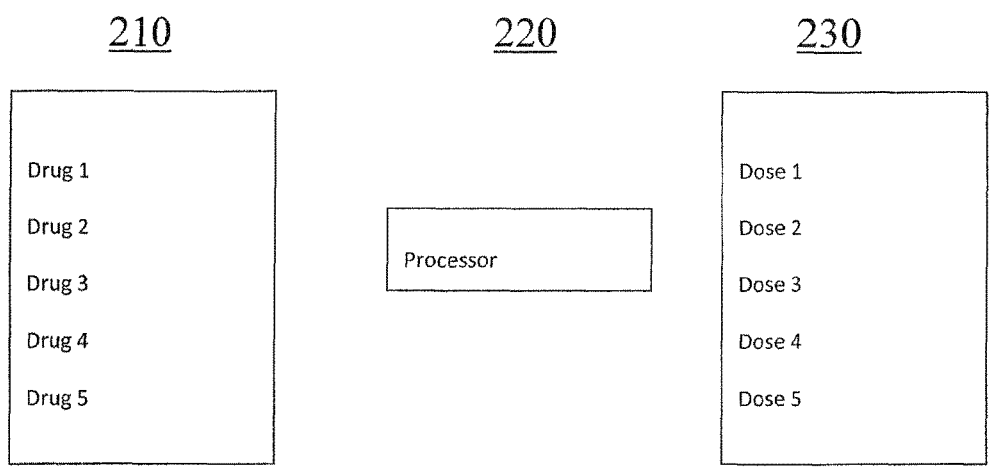
FIG. 2 is an illustration of a flow diagram for a method and system to enable the predicting of an optimal selection, combination and dosage of each of a number of component drugs for a particular patient, in accordance with an embodiment of the present disclosure.

As shown in the flow diagram of FIG. 2, the processor 104 may predict an optimal drug selection, combination and dosage of each of a number of component drugs that make up the optimal combination drug for a particular patient. Any number of drugs (e.g., Drugs 1-5 in the example of FIG. 2) may be selected (at input block 210) as optimal drugs to be combined for treating a specific patient, including but not limited to at a particular point in time, and therapeutic course. These drugs may be selected through the processes described herein, i.e. by the processor predicting, based on received patient information, the optimal drug selection and combination. Alternatively, these drugs may be selected by a prescribing medical professional and input into the computer 102.

The processor 104, after having received the selected plurality of drugs, predicts (at block 220) the optimal dosage of each component drug to be combined. As is commonly known in the relevant field, drugs often interact with other drugs, thereby enhancing effects, reducing effects, or producing side effects. Furthermore, a patient's unique physiological and health characteristics, such as diet, weight, liver function, renal function, genetic attributes, or any other patient information 110 as described above, may affect how that specific patient will react to a given drug and/or combination of drugs and other therapies.

The processor 104 will predict the optimal dosage for each component drug in the selected combination based on patient information 110 and/or reference information 114, for example as described above with respect to FIG. 1. The predicted optimal dosage(s) for each component may then be output (at output block 230) to a drug production device, where it may be combined into one or more combination drugs having the predicted optimal drug selection, combination and dosage.

Figure 3:
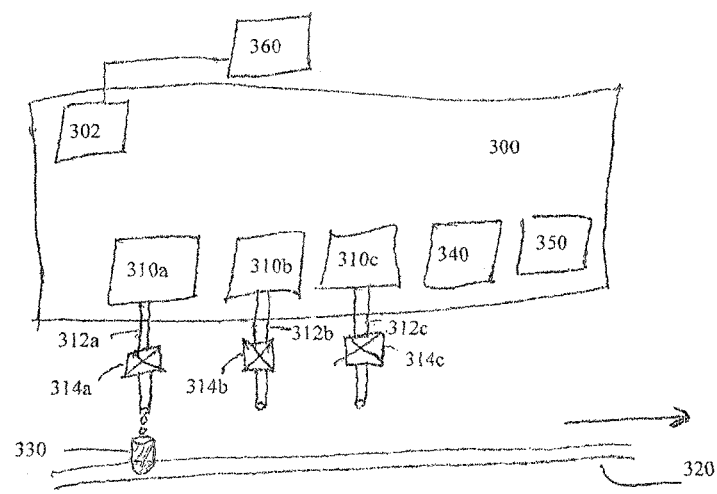
FIG. 3 is an illustration of a block diagram of a combination drug production device, in accordance with an embodiment of the present disclosure.

FIG. 3 is an illustration of a block diagram showing a combination drug production device 300, in accordance with an embodiment of the present disclosure. As described above, with respect to FIG. 1, the device 300 may receive a predicted optimal drug selection, combination and dosage directly from the processor 104, or it may receive a drug selection, combination and dosage from a licensed provider for a particular patient. For example, the device 300 may include a controller 302 which receives information from the processor 104 (FIG. 1) relating to an optimal drug combination. The controller 302 may contain control circuitry to cause the device 300 to produce the predicted drug combination based on the information received from the processor 104. Additionally, or alternatively, the drug production device 300 may produce a drug combination and dosage based on manually input information. The input may be provided by a clinician, health practitioner or any licensed provider for the patient. For example, the controller 302 may receive a particular drug combination to produce via communication with user input information, e.g. through an I/O interface and an external or internal computer. In one embodiment, the device 300 may produce a drug combination and dosage based on information input directly from a particular patient's prescribed medication list, which may be provided in an electronic format.

The drug production device 300 receives from the processor 104, or a provider, the predicted optimal or otherwise desired/prescribed drug selection, combination and dosage. Based on the received optimal drug selection, combination and dosage, the drug production device 300 produces the drug. As shown in FIG. 3, the drug production device 300 may include a plurality of drug cartridges (310a, 310 b, 310c), containing drugs 1, 2 and 3, respectively. While the device 300 is pictured having three drug cartridges (310a, 310b, 310c), more or fewer drug cartridges may be employed with the drug production devices described herein. The cartridges 310 may be removably inserted into the device 300. Each of the cartridges is coupled to a respective dispenser 312. A valve 314 is positioned in each dispenser 312, and allows drug from a respective cartridge 310 to be dispensed when the valve is open. The valves may include a meter for measuring an amount of drug passing through each dispenser 312. The meter may measure volume, weight or any other unit of measurement for an amount of drug. For example, in an embodiment, the meter counts the number of substantially equally sized units of a known quantity of a drug as they pass through the valve, using, for example, an optical particle counter as are available commercially from a variety of vendors. When the drug combining device 300 receives the predicted optimal drug selection, combination and dosage, the device 300 produces a drug product comprising a plurality of drugs by allowing the appropriate dose of each drug (e.g., drugs 1 through 3) to pass through the respective drug dispensers 312, for example by opening the respective valves 314.

The drug cartridges 314 may contain drugs in any form, including powder, solid and liquid forms. In one embodiment, the drug may be in the form of "microtablets," or small, equally sized doses of a particular drug, each microtablet having a known dosage of the drug. The microtablets may be generally spherical shaped and may be manufactured in a variety of manners, such as by freeze drying the drug and then applying a coating of ingestible collagen or some other digestible biomatrix.

The coating of each different microtablet may optionally have different colors (e.g., for identification), differing visible or invisible to human eye patterns (e.g., spots, stripes, or other ways to differentiate each microtablet). This would serve not only for identification, but potentially in verification and regulatory steps to determine and validate the components of a constructed multicomponent polypill.

The coating furthermore may be formulated specifically for each desired drug component to enable differential drug release (i.e. slow/"extended" release form) or to otherwise alter the pharmacokinetics and distribution of the drug component, different or similar to other components in the same combination polypill.

The coating could furthermore be formulated to enable drugs of differing characteristics (e.g. pH) to be in close locality without interaction of the drug components.

The drug production device 300 may further include a conveyor 320 or feeder, which conveys a drug carrier 330 through the device. The drug carrier 330 may be any type of known carrier or package for a drug, whether in liquid, solid or powder form. As shown in FIG. 3, the drug carrier 330 may be a gelatin capsule. As the carrier 330 is conveyed in the direction of the arrow, it arrives at a position beneath the dispenser for the first drug 310a (i.e., Drug 1). The predicted or desired dosage of the first drug 310a is dispensed into the carrier 330. The carrier 330 is then conveyed to the next dispenser (for drug 2), where the predicted optimal dosage of the second drug 310b may be dispensed into the carrier 330. The carrier 330 is conveyed to as many dispensers as necessary, depending on the predicted or desired/prescribed optimal drug selection, combination and dosage, with the appropriate dosage of each drug being dispensed into the carrier 330 from each dispenser. After the carrier 330 has been filled with the predicted drug combination, it is conveyed to a carrier sealer 340, which seals the carrier 330 and may further provide the carrier 330 with any desired imprints or markings. Imprints and markings may include, without limitation, the patients name, initials or other indicator, date/day of the week the carrier/pill is intended to be taken/ingested, bar codes, QR codes or other coded marking which can be read by any number of reading devices. For example, the print on an individual pill for a patient named John R. Smith may be encoded with QR or barcode data which reads: "John R. Smith, Morning Aug. 4, 2012". The encoded data (e.g., barcode or QR data) may be encrypted using any known encryption techniques. Encryption ensures patient privacy, as only authorized personnel would have access to the "key" needed to read the encrypted information. Optionally the prescriber, patient, and/or caregivers can select and 'personalize' the color, size, and shape of the carrier 330 such that it can be differentiated further from other doses, and from other individual's medications.

Optionally, a RFID type microchip, or other sensor which can track medicine compliance, may be integrated into the carrier 330, and enable remote monitoring of when the medication has been taken, and/or verify, e.g., in a hospital or care facility, through an RFID matching system incorporated into a patient's or resident's doorway or bed, that the medication is delivered to the correct patient or resident.

Also, if desired the prescribing clinician and the patient may select a custom size and shape of and color or pattern markings of a specific patient specific pill (ie. Shape, size, colors, pattern) for example a pediatric patient might choose a 'Mickey Mouse' size, shape, coloring or other markings to personalize and also differentiate from others in a similar locality.

The drug production device 300 may further include a verification stage 350, which verifies that the drug carrier 330 contains the correct dosage and combination of drugs as predicted by the processor 104, or as input by a provider, etc. The verification stage 350 may be configured to verify each, some or only a randomly selected quantity of drug carriers 330. The drug carrier 330 and/or its contents may be verified by measuring color, patterns, weight, volume, and/or mass spectrometry. For example, the verification stage 350 may include a camera (e.g., CCD, infrared, etc.), photodiodes, mass spectrometer, or any other device for measuring one or more properties of the drug carrier 330 and/or its contents and thereby verify the dosage and combination of drugs in the carrier 330. The verification stage 350 may communicate with the controller 302 and/or the processor 104 in order to compare the measured properties, or signals indicative of the measured properties, with the expected properties or signals for the determined drug combination and dosage.

The drug production device 300 may further include a scanner 360. The cartridges 310 may be provided with a barcode, RFID tag, QR code or any other indicia for communicating the contents of the cartridges 310. The scanner 360 reads the indicia provided on the cartridges 310, and communicates the scanned information to the controller 302. If the contents of the cartridges 310, as read by the scanner 360, do not match with the component drugs in the determined optimal drug combination (e.g., if the scanner reads drugs x, y and z, but the controller 302 has received a determined drug combination containing drugs x, y and a), the controller 302 will not allow the drug production device 300 to produce a drug combination.

Figure 4:
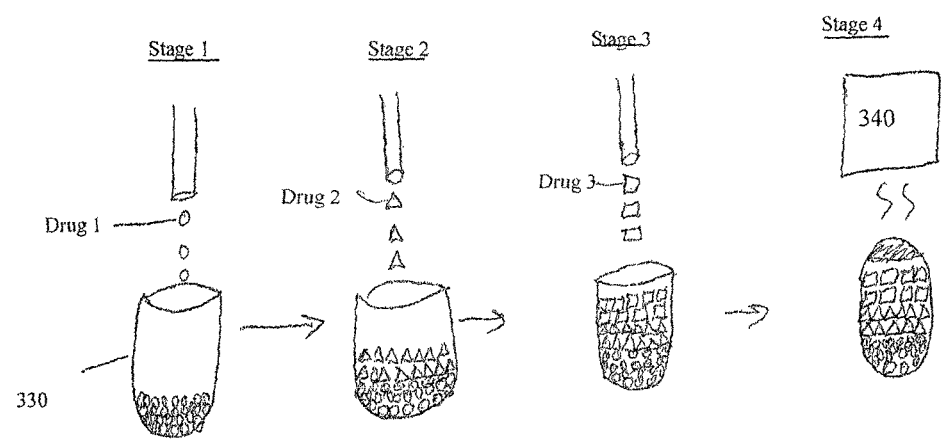
FIG. 4 and FIG. 4A are illustrations of flow diagrams for methods of filling capsules with drugs, in accordance with two embodiments of the present disclosure.

FIG. 4 shows a capsule 330 at various stages during the process of being filled by, for example, the device 300 of FIG. 3. At stage 1, the desired dosage of a first drug is dispensed into a drug carrier 330. As shown, the drug is deposited as microtablets, each spherical microtablet consisting of a specific dose of drug, e.g. 1 mg. As the first drug is being dispensed into the drug carrier 330, the meter may be counting the number of microtablets dispensed, thereby determining the dosage of the drug that is dispensed and causing the valve 314 to close when the desired dosage of drug has been dispensed. Alternatively, the drug may be in a liquid carrier, and dispensed via a pipette, into an open half capsule, or onto a porous ingestible substrate formed of a dissolvable or disintegratable fabric, paper or polymer as described, for example, in U.S. Published Application Nos. 2009/0025741A and 2010/0270257A. At stage 2, the desired dosage of a second drug is dispensed into the drug carrier 330, and the desired dosage of a third drug is dispensed into the drug carrier 330 at stage 3. At stage 4, the drug carrier 330, carrying a desired combination drug, is sealed by the sealer 340. The sealed drug carrier 330 may then pass to an optional verification stage 350.

Rather than conveying the drug carrier 330 from one dispenser 312 to the next, in one embodiment the device 300 is movable, such that the drug carrier 330 may remain stationary while the drug production device 300 moves to dispense the appropriate dosage of each drug onto or into the drug carrier 330.

Figure 4A:
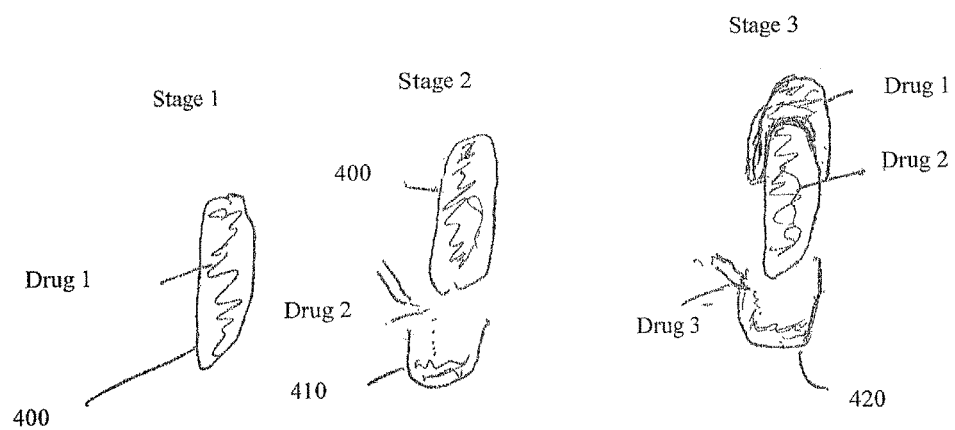

Alternatively, as shown in FIG. 4A, a first drug, which may be a liquid or powder is loaded in a first capsule 4 and the capsule sealed at stage 1. Hereafter, a second drug may be loaded into a capsule half shell 410 at a stage 2 which is press or shrink-fitted to capsule 400. The capsule may then be flipped over, and a third drug loaded into a second capsule half shell 430 at a stage 3, and press or shrink-fitted to the capsule 400 for example, according to U.S. Published Application No. 2007/0087048, the contents of which are incorporated herein by reference. The above described system has an advantage of permitting the packaging of liquid and solid drugs together, in a single dose, in which the several drugs are separated by physical barriers. Multi-compartment capsules are available commercially for example, from Micro-Dose Therapeutx, of Monmouth Junction, N.J., under the trademark "POLYCAP" capsules.

Figure 5:
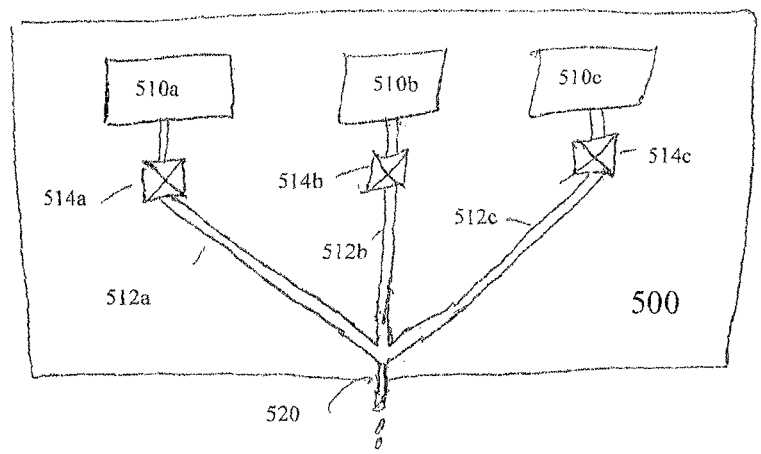
FIG. 5 is an illustration of a block diagram of a combination drug production device, in accordance with an embodiment of the present disclosure.

FIG. 5 depicts an embodiment in which the dispensing channels 512a-c for each of the drug cartridges 510a-c are all routed into a single channel 520, which dispenses the drugs onto a drug carrier 530. The drug production device 500 may include a controller, sealer, verification stage, and/or a scanner, as in the embodiment shown in FIG. 3. The valves 514a-c for each drug may be opened successively or simultaneously, with each drug being dispensed until the desired amount has been achieved (e.g., as measured by the respective meter), at which point the respective valve may be closed. As discussed with respect to the device of FIG. 3, a conveyor may be included and/or the drug production device 500 may be moveable.

In another embodiment, a plurality of drug cartridges are provided, as in the embodiment shown in FIG. 5; however, drugs from each of the cartridges may be dispensed directly into a commonly-shared funnel, from which the drugs are dispensed into or onto a drug carrier.

Figure 6:
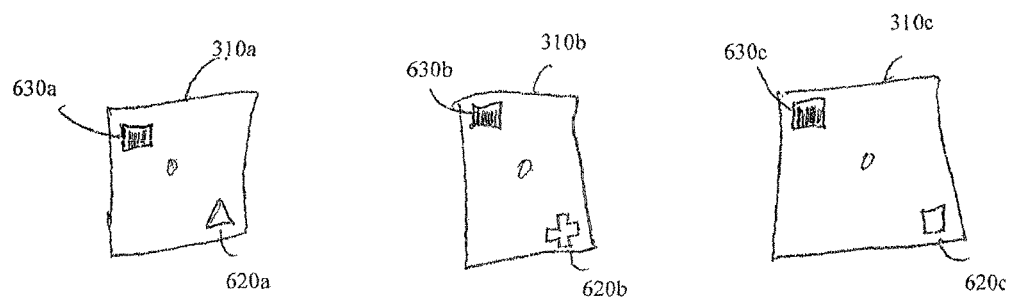
FIG. 6 is an illustration of drug cartridges, in accordance with an embodiment of the present disclosure.

Referring to FIG. 6, in order to avoid a possible mix-up of refill cartridges, the drug production device may include cartridge receiving slots, each having a unique socket for receiving a unique coupler 620a-c such that only a particular drug cartridge 310a-c may be loaded into the drug production device. The cartridge receiving slots may be removable from the drug production device and changed as needed to accommodate different drugs. Additionally, or alternatively, the cartridges 310a-c each may be provided with unique machine-readable indicia 630a-c. The indicia 630a-c may contain any number of identifiers, from words, to RFID/QR codes or other labels to identify each cartridge and for the cartridge to communicate with the device 300. Each cartridge may (e.g., similar to ink cartridges in known printing devices) communicate (e.g., over a wired, wireless or any other known network) when component drug levels are 'low' or 'empty' and may enable, trigger or remind the drug production device in which it is installed to order refills at appropriate timings depending upon usage. The cartridge may further communicate (e.g., over a wired, wireless or any other known network) with a computer located, for example, at a pharmacy or the prescribing physician's office location that it is time to authorize a refill or to examine data to determine usage or needed changes.

Figure 7A:
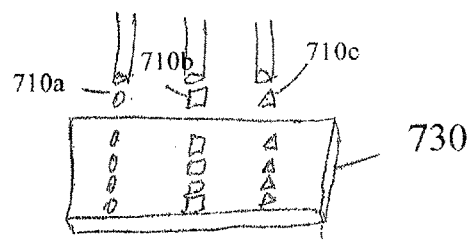
FIG. 7a is an illustration of an edible substrate containing a combination of drugs, in accordance with an embodiment of the present disclosure.
Figure 7B:
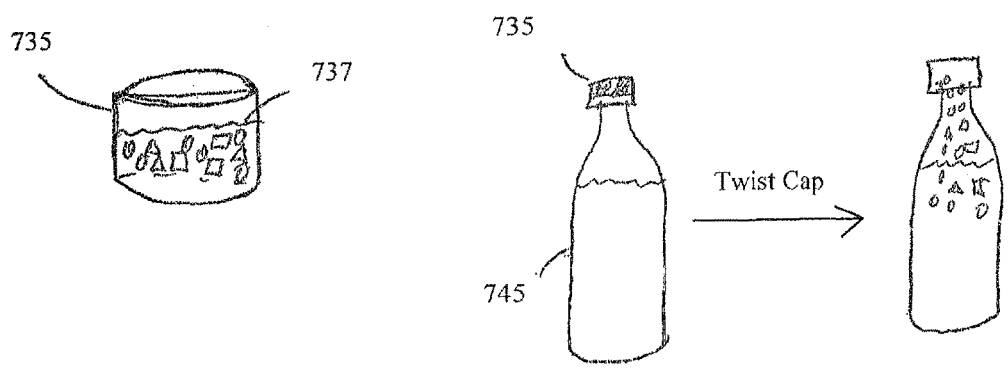
FIG. 7b is an illustration of a bottle and bottle cap containing a combination drug product, in accordance with an embodiment of the present disclosure.

The drug carrier provided by the present disclosure may be any food, liquid or edible substrate. As shown in FIG. 7a, the drug carrier may be a breakfast bar 730, and the selected combination drug and dosages may be dispensed onto (or inserted into) the bar. An edible layer (for example, chocolate or other flavored modality) may be applied over the bar 730 after the drugs 710a-c have been dispensed, to seal the drugs into the bar 730. Alternatively, as shown in FIG. 7b, the drug carrier may be a liquid contained in a bottle 745. The bottle may contain water, infant formula, a sports beverage or any other ingestible liquid. A desired dosage of drugs (e.g., in microtablet form) may be loaded into the cap 735, and a film or other frangible seal 737 provided to seal the drugs within the cap 735. When the cap 735 containing the desired dosage of drugs is twisted off of the bottle 745, the film or other frangible seal 737 is punctured and the drugs are released into the liquid.

Drugs also can be dispensed into a cap/cartridge (similar to coffee cartridges today) to hold various component/drugs, and dispensation can be controlled triggered into liquid, the patients hand directly, or other options. The system could optionally be locked and only available to specified patient, as triggered by voice, password, finger print, or other biometrics, so that the cartridge and dispensation only occurs for a desired patient. In the setting for example of drugs often abused and with addiction risk (e.g. opiates), such a system can tightly track and control the number of 'as needed' pain medications dispensed in a given time window (similar to intravenous drug 'patient controlled analgesia (PCA) devices commonly in use today).

Figure 8:
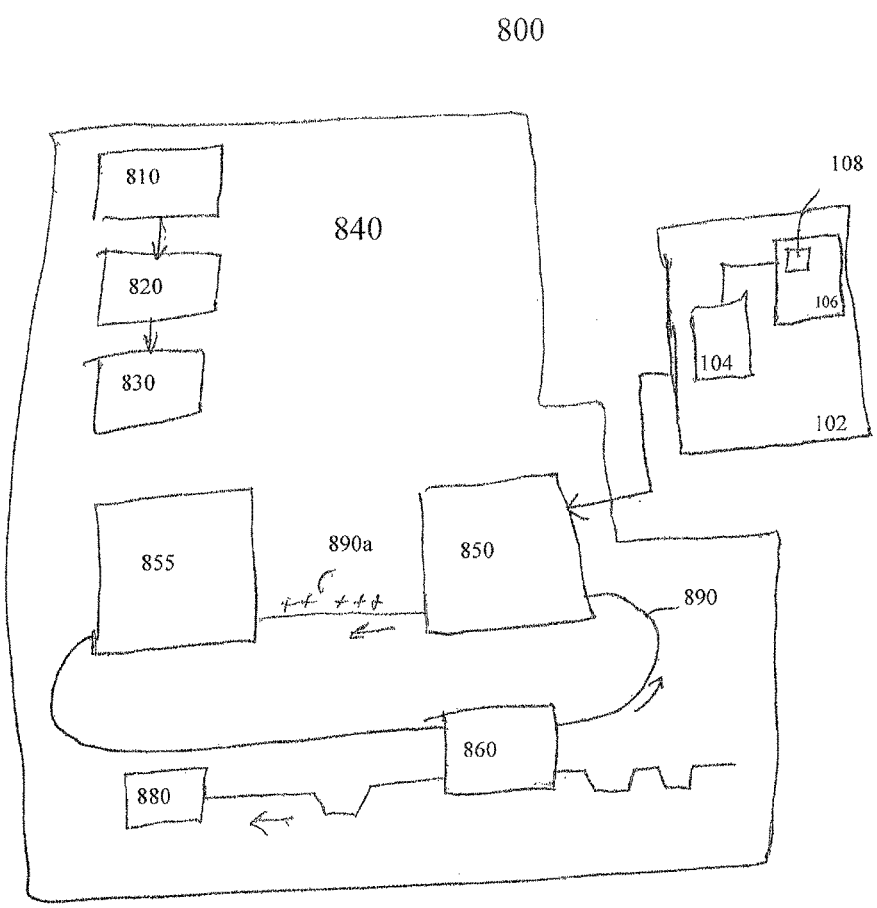
FIG. 8 is an illustration of a block diagram of a system for predicting an optimal combination drug product for a particular patient, in accordance with an embodiment of the present disclosure.

Referring now to FIG. 8, a further embodiment of a system 800 for producing a patient-specific optimal drug selection, combination and dosage is depicted. The system 800 includes a computer 102 which may have a processor 104, memory 106 and a database 108, as shown in FIG. 1 above. The system further includes a drug production device 840. The computer 102 for predicting (and/or optimizing based on patient specific feedback or from external information) an optimal drug selection, dosing and combination, as provided herein, may be employed with any known drug metering and packaging devices in order to produce a patient-specific drug. For example, U.S. Pat. Nos. 5,699,649, 5,960,609, 6,428,809, 6,702,683, 7,404,968 to Abrams et al., each of which are incorporated herein in their entirety, generally disclose devices for metering and packaging drugs. Furthermore, U.S. Pat. No. 6,923,979 to Fotland et al., incorporated herein in its entirety, discloses a method for depositing particles onto a substrate using an alternating electric field, the principles of which may generally be employed in a drug production device that receives a patient-specific optimal drug combination and dosage as provided by the present disclosure.

The drug production device 840 depicted in FIG. 8 is generally described in U.S. Pat. No. 5,699,649, and includes a supply of a powdered drug 810 which feeds into an aerosol creation element 820, where the drug powder particles are aerosolized. The particles may then be ionized at 830. A charge carrier surface 890 rotates through a surface charging station 850 where it picks up a predetermined electrostatic charge (an electrostatic "image") on a predetermined area of the carrier surface 890a. The charged surface 890a then passes through a step 855 wherein powdered drug is deposited on the carrier surface in a sufficient amount to neutralize the charge carried by the carrier surface. The predetermined amount of powder is then passed to a discharging device 860, which discharges the powder into packaging material 870. The packaging material 870 containing the predetermined amount of powder may then be sealed at 880.

In the embodiment of the present invention shown in FIG. 8, the drug production device 840 communicates with the processor 104. The processor 104 predicts the optimal drug dosage based on patient information and optionally feedback (both physiologic, subjective and objective), as described throughout the present disclosure. Once the optimal drug dosage has been determined, the processor sends a signal to the surface charging station 850 which causes the surface charging station to apply an electrostatic charge (or "image") over an appropriate predetermined surface area such that the predetermined, optimal drug dosage will be deposited onto the carrier surface at 855.

As depicted in FIG. 8, the powder drug may be discharged into packaging which is then sealed. However, in another embodiment, the powder may be discharged into an open capsule, or any other drug carrier, which is then sealed.

The drug production systems and devices provided by the present disclosure may be located at a physician's office, central pharmacy, outpatient pharmacy, hospital, nursing home or other clinical setting, or in a patient's home. They may also be optionally 'mobile' and travel with the patient.

Component drugs which make up the drug combinations as described throughout this disclosure may include, but are not limited to, the following: Aspirin; Statins and cholesterol lowering agents; AntiHypertensives of any class; Beta Blockers; Calcium Channel Blockers; ACE inhibitors; Opiates; Antibiotics, Ant-Virals; Multi Vitamin/Minerals; Amino acids; Calcium/Vitamin D; Vitamin K; DHEA; Omega 3; monococlonal antibiodies, biologics, RNA like products (i.e. RNAi) any prescription drug; any non-prescription drug; over-the-counter drugs; generic drugs and non-generics; Fish Oil; Joint supplements; "Nutriceuticals" and/or 'Green' supplements (such as extracts from vegetables, grasses, fruit etc).

Moreover, the combination drug products described herein may be composed of any form. The combination drug product, for example, may be integrated into a chewable tablet, gel (e.g., kids' "gummy"-type formulations, chocolate formulation, wafer, and/or a drink. Furthermore, the combination drug products may be packaged as individualized packets of compounded meds, which may be added to water, juice, or any other beverage. The combination drug products as provided herein may further take the form of a pill, tablet, troche, sublingual troche or lozenge, a lollipop, spray, suppository, solution, injectable (intravenous or intramuscular) compound, ophthalmic drops, or a transdermal gel or cream or patch that can be absorbed through the skin. In one embodiment, the combination drug product may be provided in a standard or optionally a programmable transdermal patch, which may be programmed to release specific drugs at particular times, or based on particular timing patterns.

Figure 9:
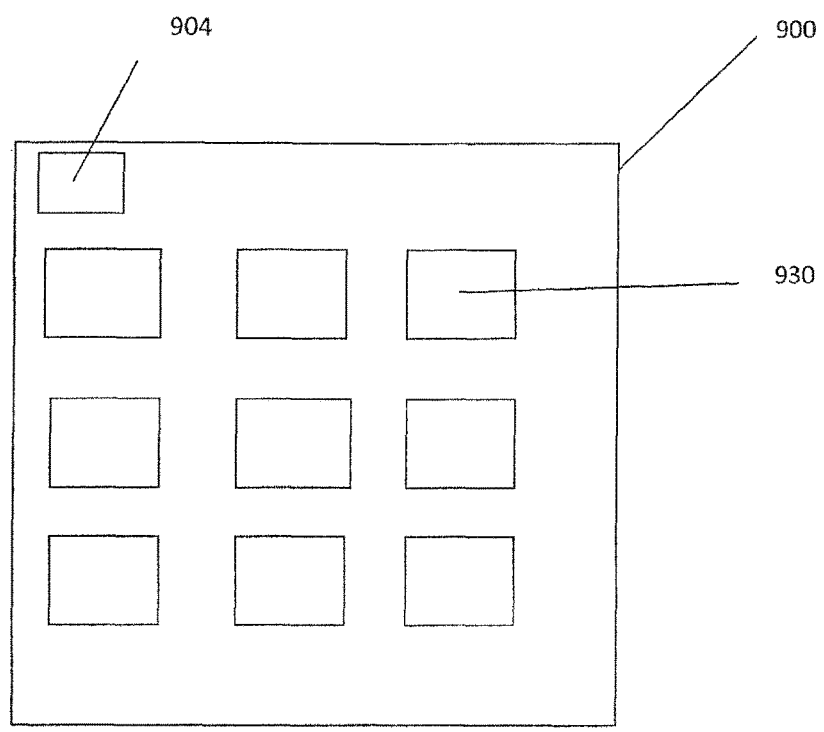
FIG. 9 is an illustration of a transdermal patch containing a plurality of drug products, in accordance with an embodiment of the present disclosure.

FIG. 9 illustrates a personalized patch 900 for transdermal delivery of a drug product. The patch 900 includes at least one drug 930, and optionally may include a plurality of drugs 930. Drugs 930 may be 'printed' or dispensed onto the patch utilizing any of the system and methods provided herein, or may be delivered onto the patch using any known methods. The drugs 930 may be absorbed into the patch 900, such that they are contained within the patch itself, or they may be contained within pockets or pouches that define boundaries between each drug product 930, as well as between the drugs 930 and the patch 900. A computer 904 or processor may further be included with the pouch, as well as circuitry between the processor and each drug compartment. The computer 904 controls the release of drugs 930 from the patch 900. Control may be accomplished, for example, by wired or wireless communication between the computer 904 and each drug compartment. When the computer 904 instructs a particular drug compartment to release a determined amount of that particular drug, the compartment may release the drug by any known transdermal patch delivery technique. In one embodiment, the patch consists of an electrically-activated, expandable material, such that upon receiving an electrical signal from the computer 904, the particular drug compartment will expand, thereby releasing a precise, predetermined dosage of drug 930.

Figure 10:
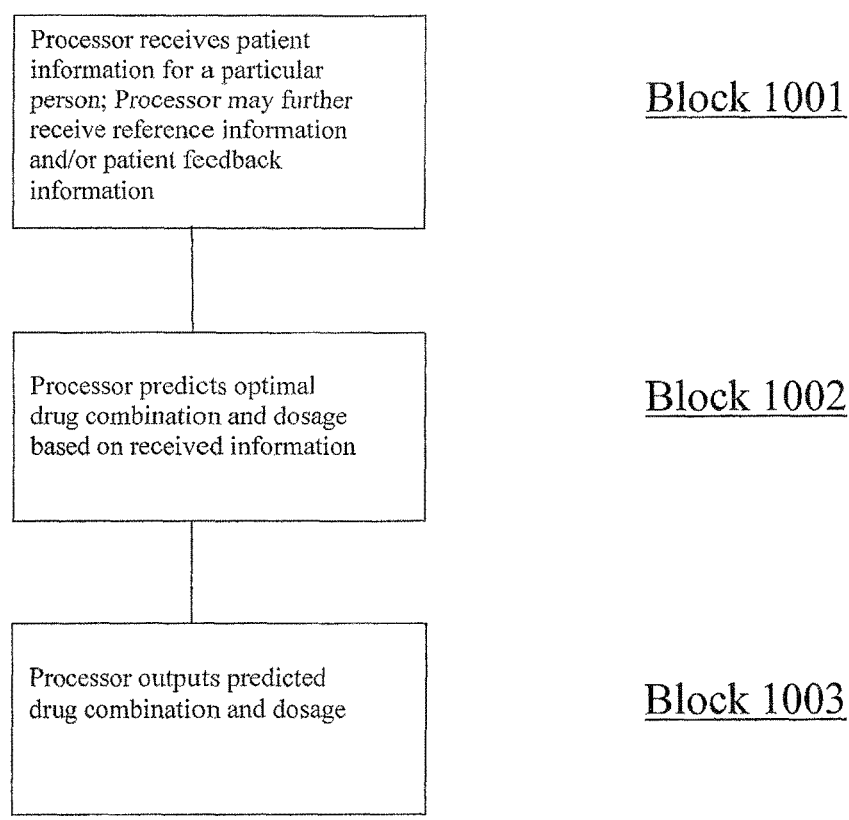
FIG. 10 is an illustration of a flow chart for a method of predicting an optimal combination drug product for a particular patient, in accordance with an embodiment of the present disclosure.

The computer 904 may further be configured to predict an optimal drug selection, combination and dosage, as described throughout this disclosure. In such a configuration, the computer 904 may control the release of drugs 930 based on the predicted optimal solution. Furthermore, the computer 904 may communicate with any external devices. For example, the computer may communicate with external measurement devices, as described in this disclosure, and may further be configured to receive patient information and/or reference information, as well as to communicate with a patient's EMR, a pharmacy and/or a display. FIG. 10 is a flow chart that illustrates a method of predicting an optimal combination drug product for a particular patient. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art. As pictured at block 1001, a processor receives patient information for a particular patient. The patient in formation may include information relating to one or more of: weight; age; sex: body mass index; metabolism; renal function; liver enzymes; pharmacokinetics; risk factors for disease; current medications; other medications; other minerals/vitamins/ supplements, history of prior side effects to one or more medications; partial or full genome SNP screening data; analysis of pharmacogenomic and/or pharmacogenetic profile; drug-drug interaction information; drug-diet interaction information; whole or partial genome analysis; vitamin deficiencies; diet; drug allergies and/or sensitivities; environmental, toxin or other allergy history; biomarker information; demographic information; patient's medical history; diagnostic information; and tissue expression profiling.

The biomarker information may include information obtained from the patient's blood, urine, sweat, saliva, body tissue, biopsy or bodily fluid.

Some of the patient information may be received from an external, ingested or implanted measurement device, which measures at least one element of patient information.

Furthermore, the processor may receive reference information and/or patient feedback information, as described herein, for example, with respect to FIG. 1. The information may be received from a variety of sources, including from any network-accessible computer device, database, server, as may further be collected 'crowd sourced' from multiple patients (e.g., information in a large healthcare system) to inform the predictions. Such a feedback loop allows the system (including the processor) to "learn" and to make more informed, and more accurate, predictions with each new piece of information fed into the system.

At block 1002, the processor predicts an optimal drug selection, combination and dosage for the patient, based on the received patient information as well as the received reference information and/or feedback information. The optimal drug selection, combination and dosage may further be predicted based on reference information, as described above, which may include information relating to the weather (e.g., for asthmatics), pollen counts, Centers for Disease control (CDC) information, medical diagnostic and statistical information, dose calculators, information from the Food and Drug Administration (FDA), and any other information which may affect a person's response to a drug. The processor may predict the optimal drug selection, be printed at home, or shipped overnight from central pharmacy etc. combination and dosage, for example, by comparing the received patient information with reference information stored in a database that relates patient information to optimal dosages of different drugs. Additionally, or alternatively, the processor may predict the optimal drug selection, combination and dosage utilizing AI or other "intelligent" computer methods and algorithms. Furthermore, the reference information may include patient feedback information, which may be, for example, directly measured by external measurement devices, as described above with respect to FIG. 1. The patient feedback information allows the AI or "intelligent" computer to "learn" and improve its predicted optimal drug selection, combination and dosage.

At block 1003, the processor outputs the determined optimal drug selection, dosing and combination. The output may be to the patient's electronic medical records, a display, and/or to a drug production device.

EXAMPLE

Example: Utilizing a Personalized Polypill after Myocardial Infarction

By way of example, the standard of care today following an acute myocardial infarction (AMI) includes medical treatment with the following
1. aspirin, clopidogrel, beta blocker, statin, ACE inhibitor (1 year therapy after myocardial infarction). We estimate that at least 1000 patients are taking this combination for every million inhabitants, every year.
2. aspirin, beta blocker, statin, ACE inhibitor (lifelong therapy)

The 2002 American College of Cardiology/American Heart Association guidelines for the management of unstable angina and non ST-segment myocardial infarction and the 2004 guidelines for ST-segment myocardial infarction assign priority to the long-term administration of four critical classes of drugs: antiplatelet agents, in particular aspirin and clopidogrel, beta-blockers, angiotensin-converting enzyme inhibitors, and statins (PMID 17701334). Approximately 1.2 million acute myocardial infarctions (AMI's) occur each year in the United States, resulting in 180,000 deaths (PMID 17922172). This means that for every million inhabitants, there is almost 4000 AMI.

Many clinical factors affect the choice of drugs e.g. (allergy to medication, liver/kidney function, drug-drug interactions, cardiovascular function, . . . ), and genetic factors-most notably those related to pharmacogenomic.

Various patient attributes if appropriately applied, could be utilized to optimize dose based on the individual patient.
Benefits of Personalized Polypill:
optimal choice of drugs based on individual's genotype—better treatment, fewer adverse drug effects
one pill with 5 different drugs—better adherence to medications Together, these factors would be very likely to significantly improve therapy and save a large amount of money for every patient on therapy.

Genetic Factors—Related to a Personalized Polypill Following an AMI
a) Clopidogrel Efficacy and CYP2C19
Clopidogrel is an antiplatelet drug. It is primarily used for disabling stent thrombosis after percutaneous coronary intervention. It is in a form of a pro-drug; therefore it needs to be activated with CYP2C19 before it can work. CYP2C19 ultra-rapid (UM) metabolizers have a higher risk of bleeding if taking normal clopidogrel dose, so a half dose is appropriate for them. On the other hand, poor metabolizers (PMs) and intermediate metabolizers (IMs) have an impaired enzyme, which is less capable of activating clopidogrel. They run a higher risk of stent thrombosis. These people should take alternative drug (e.g. prasugrel) which is not metabolised by CYP2C19.

If these therapy modifications, an estimated $50,000 per 1000 patients taking antiplatelets, and also prevent 10 deaths due to bleeding and thromboembolism.

b) Beta-Blockers
Response of several beta-blockers is affected by CYP2D6 enzyme, particularly metoprolol and carvedilol. Poor metabolisers of CYP2D6 have increased odds of bradycardia which can trigger myocardial infarction. Lower doses of beta-blockers or atenolol, which is not dependent on CYP2D6 enzyme should be used in CYP2D6 PMs. (PMID 18784654).

c) Statins
The main adverse effect of statins is myopathy. Atorvastatin and particularly simvastatin are affected by polymorphisms in SLCO1B1 gene. 2% people, who are minor homozygotes have 17 times higher odds of myopathy, while heterozygotes have 4, 5 times higher odds of myopathy compared to common homozygotes. Patients with higher odds could minimize their risk if they would take other statins (rosuvastatin, fluvastatin).

d) ACE Inhibitors
A study showed that 3 SNPs affect perindopril response. 25% of people carry 3 or more variant alleles and do not have treatment benefit with perindopril. If these people took different drugs, they could have higher benefit in preventing cardiovascular disease.

Our economic analysis showed that genotyping prior clopidogrel treatment is cost effective. Cost of genotyping for additional SNPs that affect other drugs and treatment choices would not be substantially higher, but benefits for patients and health care payers would be substantially higher.

Effect of Better Adherence
Study showed that adherence to cardiovascular drugs falls with number of concurrent prescribed drugs (PMID 20351303 Medication adherence in cardiovascular disease, Circulation, 2010)

| medication | self-reported adherence % |
|---|---|
| aspirin | 83 |
| lipid lowering agents | 63 |
| beta blockers | 61 |
| aspirin + beta blocker | 54 |
| aspirin + beta blocker + lipid lowering agent | 39 |

Compliance is likely to be higher if all drugs would be combined in a single polypill. Additionally, these drugs would have fewer adverse drug reactions due to choice of drugs based on individual's genetic background. Adverse drug reactions are frequent cause of non-adherence to drugs—because drugs would be chosen based on individual's genotype, adverse drug reactions would be present in much lower frequencies). Therefore we estimate that adherence to polypill would be close to ideal (>80%).

According to study (PMID 15908846), if adherence is optimal (>80%) one would save compared to suboptimal adherence (20-39%):

| adherence level | hypertension | hypercholesterolemia |
|---|---|---|
| 20-39 | 6062 | 4999 |
| >80 | 4871 | 3924 |
| savings | 1191 | 1075 |

Another study showed (PMID 16603580) that patients, who do not take drugs after nonfatal myocardial infarction, have significantly decreased survival than patients who take 4 drugs (aspirin, ACE inhibitor, beta blocker and statin).

Therefore, we estimate, that for every patient on a cardiovascular polypill one could save approximately $1000 every year, despite additional drug costs. In the first year the economic benefits would be even higher due to choice of optimal antiplatelet (clopidogrel/prasugrel) despite the cost of genotyping.

Post-myocardial infarction patients who discontinue their prescribed aspirin, statin, and beta-blocker are more than three times more likely to die than patients who remain adherent. The economic impact of non-adherence is also enormous. At least a third of all medication-related hospital admissions are caused by poor medication adherence, 21 and these events alone are estimated to cost $100 billion annually in the USA. (PMID 18183470)

For every 1000 patients on polypill for cardiovascular diseases one could save approximately 1 million dollars due to optimal treatment, fewer adverse drug reactions, higher adherence.

Various changes may be made in the invention without departing from the spirit and the scope thereof.

For example, while the drugs have been described as being a liquid form or powder form, the drugs may be provided in a variety of forms including microencapsulated forms which optionally may include time release coatings, freeze dried, coated with ingestible collagen or other digestible biomatrix. The drugs may also be formed as pressed tablets or the like which are fixed together to form a caplet or tablet. The drugs may be liquid, gels, patches or other fast or sustained released compounded components designed to be dropped, placed on or near the patient's eye(s).

Also, as illustrated in detail in Appendix A, incorporated herein by reference, the present disclosure permits a clinician/prescriber to transmit information about drugs/doses, etc., in a personalized pill, along with other standard meds which might be prescribed in conjunction, for example a proprietary/non generic pill. This information and timing information is transmitted to the patient electronically, thru cloud, web/wifi, etc., to device such as mobile phone or tablet, or bedside or bathroom sink display or device to include 'When' to take the personalized and other med, and how, e.g., with food, such that compliance, adherence reminders are provided to the patient and/or caregivers.

This enabled tracking of compliance/adherence, and feedback on adherence to the patient and caregivers, optionally in real time, i.e. a patient's mother, in the case of a child, is texted or otherwise informed when patient has taken, or has missed a dose or multiple doses. This tracking can be done via manual entry of 'dose taken' i.e. via phone app or via any number of medical dispensers, such as described in U.S. Published Patent Application No. 20070016443A, the contents of which are incorporated hereby reference. The 'app' on the patient's device or devices can allow integration of wearable/external device information (i.e. vital signs or blood glucose) and also subjective symptoms and side effects. This enables feedback further to inform future individualized or standard drug regimen dosing.

Also, the clinician may elect to do programmed/iterative 'smart prescription' as opposed to emperic or even primary dosing recommendations. This enables the clinician to prescribe, for example, a low dose of a blood pressure agent (such as beta blocker) and to follow actual blood pressure measures, and based on the BP results, iterate on the next version of the personalized pill or standard pills. For example, if evening BPs are running above targets an evening dose of the beta blocker or additional anti-hypertensive could be added to the regimen, either at that same time the pill is manufactured on site) or on next versions shipped or sent from central or local pharmacy.

The idea here is a "decision" tree algorithm +/–AI, that would enable the actual script itself to "titer up or down" or add as needed based on various feedback", such that there is an option to be free of multiple calls to physician, etc.

The disclosure also permits one to have an "app" that enables tracking of personalized and other meds (optional connection to a dispenser) with feedback on compliance and insight by the patient to see their values, (BPS, glucose, weight, sleep information, etc. quantified self type data.

Appendix B shows five (5) patients, with different attributes, and how their drugs should differ.

It should be emphasized that the above-described embodiments of the present systems and methods for the production of a personalized drug product are merely possible examples of implementations and are merely set forth for a clear understanding of the principles of the invention. Many different embodiments of the systems, methods and devices described herein may be designed and/or fabricated without departing from the spirit and scope of the invention. All these and other such modifications and variations are intended to be included herein within the scope of this disclosure and protected by the following claims. Therefore the scope of the invention is not intended to be limited except as indicated in the appended claims.

What is claimed is:

1. A system for producing a drug product for an individual patient, comprising:
   a computer processor configured to receive information relating to the patient and to predict, based on the received patient information, an optimal drug selection, combination drug product comprising a plurality of discrete units of a first drug and a plurality of discrete units of a second drug, and dosage for the patient; and
   a drug production device, in communication with the processor, for producing the drug product based on the predicted optimal drug selection, combination drug product, and dosage, wherein the drug production device comprises:
   a plurality of drug containers, each configured to hold a quantity of a drug in the form of microtablets, each microtablet containing an equal sized dose of a particular drug, each microtablet being coated so as to enable drugs of different pH to be in close locality without interaction of components of the combination drug product, and each having a unique coupling element to couple the drug container to the drug production device;
   a plurality of drug dispensers, each of said drug dispensers coupled to one of said drug containers;
   a supply of empty ingestible capsules;
   a controller, which controls dispensing by count of said microtablets of a drug by each drug dispenser into the ingestible capsules;

a verification unit including a scanner for scanning identifying indicia provided on the drug containers and comparing the indicia to the predicted optimal drug selection and combination drug product, wherein the combination drug product comprises at least a first coated microtablet of a first drug and a second coated microtablet of a second drug, wherein the second drug is distinct from the first drug, in a closed unitary ingestible capsule package customized for the patient produced from selected dispensed drugs, wherein the patient information includes information selected from (1) at least one of the group consisting of: weight; age; sex; BSA (body surface area); body mass index; lean body mass, percentage body fat, metabolism; renal function; liver enzymes; proteomics/biomarkers, blood chemistries, pharmacokinetics; risk factors for disease; partial or full genome SNP screening data; whole or partial genome analysis; vitamin deficiencies; vitamin and micronutrient levels; diet; environmental, toxin or other allergy history; the patient's medical history; diagnostic information; exercise activity; sleep activities; tissue expression profiling; hormonal cycles, biomarker information; radiologic/imaging information, demographic information; monthly reproductive cycle; geolocation, social network, consumer information, habits, physiologic data, electroencephalogram (EEG) recordings, behavioral history, geographic history, exposures or potential exposures to toxins and other environmental factors including exposure to radiation, compliance history and personality testing from body measurement devices, and (2) at least one of the group consisting of current medications; other medications/supplements; history of prior side effects to one or more medications; analysis of pharmacogenomic and/or pharmacogenetic profile; drug-drug interaction information; drug-diet interaction information; and drug allergies and/or sensitivities; and a conveyor for moving an ingestible capsule to successive drug dispensers, wherein a determined quantity of each drug is dispensed into the ingestible capsule from each drug dispenser.

2. The system of claim 1, wherein the biomarker information comprises information obtained from the at least one of the group consisting of the patient's blood, urine, sweat, saliva, body tissue, biopsy or bodily fluid.

3. The system of claim 1, wherein the processor further receives reference information and predicts the optimal drug selection, combination drug product, and dosage for the patient based on the received patient information and reference information.

4. The system of claim 1, further comprising an external measurement device, said external measurement device being configured to measure at least one element of patient information, and to transmit said measured element of patient information to the processor.

5. The system of claim 1, further comprising a database configured to store a plurality of categories of information that relates patient information to optimal dosages of different drugs, and said processor predicts an optimal drug selection, combination drug product, and dosage for the patient by comparing the received patient information with the information stored in the database.

6. The system of claim 1, wherein the predicted optimal drug selection, combination drug product, and dosage is output to a display.

7. The system of claim 1, wherein the processor is housed within the drug production device.

8. The system of claim 1, wherein the predicted optimal drug selection, combination drug product, and dosage is transmitted to the patient's electronic medical record.

9. The system of claim 1, wherein the predicted optimal drug selection, combination drug product, and dosage is transmitted to a pharmacy.

10. The system of claim 1, wherein the processor is configured to communicate with the drug production device over a wireless network.

11. The system of claim 1, wherein the processor further receives patient feedback information and predicts the optimal drug selection, combination drug product, and dosage for the patient based on the received patient information and the patient feedback information.

12. The system of claim 1, wherein said combination drug product is produced based on information received from a processor relating to a predicted optimal drug selection, combination drug product, and dosage.

13. The system of claim 1, wherein each of said drug dispensers are coupled to one another.

14. The system of claim 1, wherein the microtablets are colored.

15. The system of claim 1, wherein the microtablets are patterned.

16. A method for producing a custom, optimal combination drug product for an individual patient, comprising:
receiving, by a processor, information relating to the patient;
predicting, by the processor, an optimal drug selection, combination drug product comprising a plurality of discrete units of a first drug and a plurality of discrete units of a second drug, and dosage for the patient, based on said received patient information;
outputting the predicted optimal drug selection, combination drug product, and dosage for the particular patient to a drug production device which comprises:
a plurality of drug containers, each configured to hold a quantity of a drug in the form of microtablets, each microtablet containing an equal sized dose of a particular drug, each microtablet being coated so as to enable drugs of different pH to be in close locality without interaction of components of the combination drug product, and each drug container having a unique coupling element to couple the drug container to the drug production device;
a plurality of drug dispensers, each of said drug dispensers coupled to one of said drug containers;
a supply of empty ingestible capsules;
a controller, which controls dispensing by count of said microtablets of a selected drug or drugs by each drug dispenser into the ingestible capsules;
a conveyor for moving an ingestible capsule to successive drug dispensers, wherein a determined quantity of each drug is dispensed into the ingestible capsule from each drug dispenser; and
a verification unit including a scanner for scanning identifying indicia provided on the drug containers and comparing the indicia to the predicted optimal drug selection and combination drug product,
dispensing a controlled amount of selected drugs comprising at least a first coated microtablet of a first drug and a second coated microtablet of a second drug, wherein the second drug is distinct from the first drug, via the controller, into an empty ingestible capsule, closing the capsule using the drug production device to produce a closed unitary ingestible capsule package comprising the combination drug product customized for said individual patient, wherein the patient information includes information selected from (1) at least one of the group consisting of: weight; age; sex; BSA (body surface area); body mass index; lean body mass, percentage body fat, metabolism; renal function; liver enzymes; proteomics/biomarkers, blood chemistries, pharmacokinetics; risk factors for disease; partial or full genome SNP screening data; whole or partial genome analysis; vitamin deficiencies; vitamin and micronutrient levels; diet; environmental, toxin or other allergy history; the patient's medical history; diagnostic information; exercise activity; sleep activities; tissue expression profiling; hormonal cycles, biomarker information; radiologic/imaging information, demographic information; monthly reproductive cycle; geolocation, social network, consumer information, habits, physiologic data, electroencephalogram (EEG) recordings, behavioral history, geographic history, exposures or potential exposures to toxins and other environmental factors including exposure to radiation, compliance history and personality testing from body measurement devices, and (2) at least one of the group consisting of current medications; other medications/supplements; history of prior side effects to one or more medications; analysis of pharmacogenomic and/or pharmacogenetic profile; drug-drug interaction information; drug-diet interaction information; and drug allergies and/or sensitivities.

17. The method of claim 16, wherein the biomarker information comprises information obtained from the at least one of the patient's blood, urine, sweat, saliva, body tissue, biopsy or bodily fluid.

18. The method of claim 16, wherein at least a portion of said received patient information is received from an external measurement device, said device being configured to measure at least one element of patient information, and to transmit said measured element of patient information to the processor.

19. The method of claim 16, wherein at least a portion of said received patient information includes patient-reported information relating to the severity of symptoms and/or side effects.

20. The method of claim 16, wherein said processor predicts the optimal drug selection, combination drug product, and dosage by comparing the received patient information with information stored in a database that relates patient information to optimal dosages of different drugs.

21. The method of claim 16, further comprising:
outputting the predicted optimal drug selection, combination drug product, and dosage to a display.

22. The method of claim 16, wherein the processor is housed within the drug production device.

23. The method of claim 16, further comprising: transmitting the predicted optimal drug selection, combination drug product, and dosage to the patient's electronic medical record.

24. The method of claim 16, wherein the processor is configured to communicate with the drug production device over a wireless network.

25. The method of claim 16, wherein the microtablets are colored.

26. The method of claim 16, wherein the microtablets are patterned.

27. A non-transitory computer readable medium containing instructions to cause a computing device to perform a method comprising:
receiving, by a processor, information relating to a patient;
predicting, by the processor, an optimal drug selection, combination drug product comprising a plurality of discrete units of a first drug and a plurality of discrete units of a second drug, and dosage for said patient, based on said received patient information;
outputting the predicted optimal drug selection, combination drug product, and dosage for the particular patient to a drug production device which comprises:
a plurality of drug containers, each configured to hold a quantity of a drug in the form of microtablets containing equally sized doses of a particular drug, each microtablet being coated so as to enable drugs of different pH to be in close locality without interaction of components of the combination drug product, and each drug container having a unique coupling element to couple the drug container to the drug production device;
a plurality of drug dispensers, each of said drug dispensers coupled to one of said drug containers;
a supply of empty ingestible capsules;
a controller, which controls dispensing by count of said microtablets of a selected drug or drugs by each drug dispenser into the ingestible capsules;
a conveyor for moving an ingestible capsule to successive drug dispensers, wherein a determined quantity of each drug is dispensed into the ingestible capsule from each drug dispenser, and
a verification unit including a scanner for scanning identifying indicia provided on the drug containers and comparing the indicia to the predicted optimal drug selection and combination drug product,
dispensing a controlled amount of selected drugs comprising at least a first coated microtablet of a first drug and a second coated microtablet of a second drug, wherein the second drug is distinct from the first drug, via the controller, into an unfilled ingestible capsule, and
closing the capsule using the drug production device to produce a closed unitary ingestible capsule package comprising the combination drug product customized for said individual patient, wherein the patient information includes information selected from (1) at least one of the group consisting of: weight; age; sex; BSA (body surface area); body mass index; lean body mass, percentage body fat, metabolism; renal function; liver enzymes; proteomics/biomarkers, blood chemistries, pharmacokinetics; risk factors for disease; partial or full genome SNP screening data; whole or partial genome analysis; vitamin deficiencies; vitamin and micronutrient levels; diet; environmental, toxin or other allergy history; the patient's medical history; diagnostic information; exercise activity; sleep activities; tissue expression profiling; hormonal cycles, biomarker information; radiologic/imaging information, demographic information; monthly reproductive cycle; geolocation, social network, consumer information, habits, physiologic data, electroencephalogram (EEG) recordings, behavioral history, geographic history, exposures or potential exposures to toxins and other environmental factors including exposure to radiation, compliance history and personality testing from body measurement devices, and (2) at least one of the group consisting of current medications; other medications/supplements; history of prior side effects to one or more medications; analysis of pharmacogenomic and/or pharmacogenetic profile; drug-drug interaction information; drug-diet interaction information; and drug allergies and/or sensitivities.

28. The non-transitory computer readable medium of claim 27, wherein the biomarker information comprises information obtained from at least one of the patient's blood, urine, sweat, saliva, body tissue, biopsy or bodily fluid.

29. The non-transitory computer readable medium of claim 27, wherein at least a portion of said received patient information is received from an external measurement device, said device being configured to measure at least one element of patient information, and to transmit said measured element of patient information to the processor.

30. The non-transitory computer readable medium of claim 27, further comprising second program instructions, wherein said processor predicts the optimal drug selection, combination drug product, and dosage by comparing the received patient information with information stored in a database that relates patient information to optimal dosages of different drugs.

31. The non-transitory computer readable medium of claim 27, further comprising third program instructions for outputting the predicted optimal drug selection, combination drug product, and dosage to a display.

32. The non-transitory computer readable medium of claim 27, wherein the processor is housed within the drug production device.

33. The non-transitory computer readable medium of claim 27, further comprising fourth program instructions for transmitting the predicted optimal drug selection, combination drug product, and dosage to the patient's electronic medical record.

34. The non-transitory computer readable medium of claim 27, wherein the processor is configured to communicate with the drug production device over a wireless network.

35. The non-transitory computer readable medium of claim 27, wherein the microtablets are colored.

36. The non-transitory computer readable medium of claim 27, wherein the microtablets are patterned.

* * * * *